US 11,737,712 B2

(12) United States Patent
Greenhut et al.

(10) Patent No.: US 11,737,712 B2
(45) Date of Patent: Aug. 29, 2023

(54) MEDICAL DEVICE AND METHOD FOR DETECTING ELECTRICAL SIGNAL NOISE

(71) Applicant: Medtronic, Inc., Minneapolis, MN (US)

(72) Inventors: Saul E. Greenhut, Denver, CO (US); Yuanzhen Liu, Minneapolis, MN (US); Xusheng Zhang, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 218 days.

(21) Appl. No.: 16/874,920

(22) Filed: May 15, 2020

(65) Prior Publication Data

US 2021/0353233 A1    Nov. 18, 2021

(51) Int. Cl.
| | |
|---|---|
| *A61B 5/363* | (2021.01) |
| *A61B 5/00* | (2006.01) |
| *A61B 5/316* | (2021.01) |
| *A61N 1/365* | (2006.01) |

(52) U.S. Cl.
CPC ............ *A61B 5/7203* (2013.01); *A61B 5/316* (2021.01); *A61B 5/363* (2021.01); *A61B 5/4836* (2013.01); *A61B 5/7221* (2013.01); *A61N 1/365* (2013.01)

(58) Field of Classification Search
CPC .............................. A61B 5/7203; A61B 5/363
USPC ........................................................ 600/518
See application file for complete search history.

(56) References Cited

U.S. PATENT DOCUMENTS

| | | | |
|---|---|---|---|
| 8,437,842 B2 | 5/2013 | Zhang et al. | |
| 8,825,145 B1 * | 9/2014 | Zhang .................... | A61B 5/366 600/521 |
| 9,364,162 B2 | 6/2016 | Cao et al. | |
| 9,375,181 B2 | 6/2016 | Hemming et al. | |
| 9,566,012 B2 | 2/2017 | Greenhut et al. | |
| 9,808,640 B2 | 11/2017 | Zhang | |
| 10,154,794 B2 | 12/2018 | Stadler et al. | |
| 10,226,197 B2 | 3/2019 | Reinke et al. | |
| 10,252,068 B2 | 4/2019 | Gunderson et al. | |
| 10,252,071 B2 | 4/2019 | Cao et al. | |
| 10,406,373 B2 | 9/2019 | Zhang | |
| 10,470,681 B2 | 11/2019 | Greenhut et al. | |
| 10,583,306 B2 | 3/2020 | Zhang et al. | |
| 2010/0249627 A1 | 9/2010 | Zhang et al. | |
| 2010/0312131 A1 | 12/2010 | Naware et al. | |

(Continued)

OTHER PUBLICATIONS

PCT International Search Report and Written Opinion for International Application No. PCT/US2021/030603 dated Aug. 4, 2021 (11 pages).

*Primary Examiner* — Nicole F Lavert
*Assistant Examiner* — Nicole F Johnson

(57) ABSTRACT

A medical device is configured to sense event signals from a cardiac electrical signal and determine maximum amplitudes of cardiac electrical signal segments associated with sensed event signals. The medical device is configured to determine at least one tachyarrhythmia metric based on at least a greatest one of the determined maximum amplitudes. The medical device may determine when the at least one tachyarrhythmia metric does not meet true tachyarrhythmia evidence and, in response, determine when the maximum amplitudes meet suspected noise criteria. The medical device may withhold a tachyarrhythmia detection and tachyarrhythmia therapy when suspected noise criteria are met.

25 Claims, 15 Drawing Sheets

(56) References Cited

U.S. PATENT DOCUMENTS

| | | | |
|---|---|---|---|
| 2015/0306408 A1* | 10/2015 | Greenhut | A61B 5/363 607/5 |
| 2016/0113536 A1* | 4/2016 | Greenhut | A61B 5/316 600/512 |
| 2016/0158567 A1 | 6/2016 | Marshall et al. | |
| 2018/0028085 A1 | 2/2018 | Zhang et al. | |
| 2018/0028828 A1* | 2/2018 | Cao | A61N 1/3925 |
| 2018/0207436 A1 | 7/2018 | Zhang | |
| 2018/0303368 A1* | 10/2018 | Zhang | A61N 1/36585 |
| 2019/0184164 A1* | 6/2019 | Zhang | A61N 1/36592 |
| 2020/0178830 A1 | 6/2020 | Zhang et al. | |

* cited by examiner

MEDICAL DEVICE AND METHOD FOR DETECTING ELECTRICAL SIGNAL NOISE

TECHNICAL FIELD

The disclosure relates generally to a medical device and method for detecting electrical signal noise.

BACKGROUND

Medical devices may sense electrophysiological signals from the heart, brain, nerve, muscle or other tissue. Such devices may be implantable, wearable or external devices using implantable and/or surface (skin) electrodes for sensing the electrophysiological signals. In various medical devices or medical device systems, implantable, transcutaneous, or cutaneous (skin) electrodes may be positioned for sensing an electrophysiological signal by the medical device, which may be an implantable, external or wearable medical device. Such devices may include devices configured to monitor an electrophysiological signal for a medical condition or health purposes (including, but not limited to fitness trackers, watches, or other medical or fitness devices).

In some cases, such devices may be configured to deliver a therapy based on the sensed electrophysiological signals. For example, implantable or external cardiac pacemakers, cardioverter defibrillators, cardiac monitors and the like, sense cardiac electrical signals from a patient's heart. A cardiac pacemaker or cardioverter defibrillator may deliver therapeutic electrical stimulation to the heart via electrodes carried by one or more medical electrical leads and/or electrodes on a housing of the medical device. The electrical stimulation may include signals such as pacing pulses or cardioversion or defibrillation shocks. In some cases, a medical device may sense cardiac electrical signals attendant to the intrinsic or pacing-evoked depolarizations of the myocardium and control delivery of stimulation signals to the heart based on the sensed cardiac electrical signals attendant to the myocardial depolarizations. Upon detection of an abnormal rhythm, such as bradycardia, tachycardia or fibrillation, an appropriate electrical stimulation signal or signals may be delivered to restore or maintain a more normal rhythm of the heart. For example, an implantable cardioverter defibrillator (ICD) may deliver pacing pulses to the heart of the patient upon detecting bradycardia or tachycardia or deliver cardioversion or defibrillation (CV/DF) shocks to the heart upon detecting tachycardia or fibrillation.

A medical device may sense cardiac electrical signals from a heart chamber and deliver electrical stimulation therapies to the heart chamber using electrodes carried by a transvenous medical electrical lead. Cardiac signals sensed within a heart chamber using endocardial electrodes, for example, generally have a high signal strength and quality for reliably sensing near-field cardiac electrical events, such as ventricular R-waves sensed from within a ventricle, but may still be corrupted by noise such as electromagnetic interference (EMI), noise signals due to lead issues, or other non-cardiac electrical signal noise. In some proposed or available ICD systems, an extra-cardiac lead may be coupled to the ICD, in which case cardiac signal sensing from outside the heart may present challenges in reliably sensing cardiac electrical event signals, particularly in the presence of environmental or non-cardiac electrical signal noise.

SUMMARY

In general, the disclosure is directed to a medical device and techniques for determining noise corruption of an electrophysiological signal sensed by the medical device. The techniques disclosed herein may be used in conjunction with a variety of cardiac monitoring and/or therapy delivery devices, including devices that monitor a patient heart rate for detecting tachyarrhythmia. For example, a determination of noise present in a cardiac electrical signal may be included in heart rate monitoring and tachyarrhythmia detection methods to avoid false tachyarrhythmia detection due to the presence electrical noise, such as electromagnetic interference (EMI), non-cardiac myopotential signals or other electrical noise signals. A device operating according to the techniques disclosed herein may determine when the amplitude of signals associated with event signals sensed as cardiac events meet suspected noise criteria. The medical device may determine a tachyarrhythmia metric based on at least a greatest maximum amplitude signal. The medical device may determine one or more interval-based tachyarrhythmia metrics and/or one or more morphology-based tachyarrhythmia metrics. The medical device may determine when true tachyarrhythmia evidence criteria are met based on the tachyarrhythmia metric(s). When the true tachyarrhythmia evidence criteria are unmet and the suspected noise criteria are met, the medical device may determine noise corruption of the cardiac electrical signal. Determination of noise may be used to withhold a tachyarrhythmia detection by the medical device even when other tachyarrhythmia detection criteria, such as rate based criteria, are met. In this way, delivery of unnecessary therapy, such as a CV/DF shock, may be avoided when tachyarrhythmia might otherwise be falsely detected due to noise corruption of the cardiac electrical signal.

In some examples, a medical device as disclosed herein may be configured to detect ventricular tachyarrhythmia, e.g., ventricular tachycardia (VT) or ventricular fibrillation (VF), based on detecting a ventricular rate that is faster than a tachyarrhythmia detection rate for at least a predetermined number of ventricular cycles. The VT or VF rate may be detected by sensing R-waves from a cardiac electrical signal, determining ventricular intervals or RR intervals (RRIs) between consecutively sensed R-waves, and counting the number of ventricular intervals that are shorter than VT or VF detection intervals. Non-cardiac noise may be oversensed as ventricular R-waves due to cardiac signal amplitude variability and/or due to episodes of non-cardiac noise. Oversensing of non-cardiac noise may cause the medical device to falsely increase the count of VT or VF intervals when an underlying normal sinus rhythm may be present. A medical device operating according to the techniques disclosed herein may determine noise corruption of a cardiac electrical signal, which may be occurring during a series of ventricular intervals that include tachyarrhythmia detection intervals.

In one example, the disclosure provides a medical device including a sensing circuit and a control circuit coupled to the sensing circuit. The sensing circuit may be configured to sense at least one cardiac electrical signal and sense event signals from the at least one cardiac electrical signal. The control circuit may be configured to determine a maximum amplitude associated with each one of multiple sensed event signals, identify a greatest maximum amplitude from the determined maximum amplitudes and determine at least one tachyarrhythmia metric based on at least the identified greatest maximum amplitude. The control circuit may be further configured to determine the at least one tachyarrhythmia metric does not meet true tachyarrhythmia evidence criteria and, in response to the at least one tachyarrhythmia metric not meeting true tachyarrhythmia evidence criteria, determine that suspected noise criteria are met based on the determined maximum amplitudes. The control circuit may determine that a tachyarrhythmia detection criterion is met based on event signals sensed by the sensing circuit and, in response to determining that suspected noise criteria are met, withhold a tachyarrhythmia detection when the tachyarrhythmia detection criterion is determined to be met.

In another example, the disclosure provides a method including sensing at least one cardiac electrical signal, sensing event signals from the at least one cardiac electrical signal and determining a maximum amplitude associated with each one of multiple sensed event signals. The method may further include identifying a greatest maximum amplitude from the determined maximum amplitudes, determining at least one tachyarrhythmia metric based on at least the identified greatest maximum amplitude, and determining the at least one tachyarrhythmia metric does not meet true tachyarrhythmia evidence criteria. In response to the at least one tachyarrhythmia metric not meeting true tachyarrhythmia evidence criteria, the method may include determining that suspected noise criteria are met based on the determined maximum amplitudes. The method may further include determining that a tachyarrhythmia detection criterion is met based on the plurality of sensed event signals. In response to determining that suspected noise criteria are met, the method may include withholding a tachyarrhythmia detection when the tachyarrhythmia detection criterion is determined to be met.

In another example, the disclosure provides a non-transitory computer-readable medium storing a set of instructions which, when executed by a control circuit of a medical device, cause the medical device to sense at least one cardiac electrical signal, sense event signals from the at least one cardiac electrical signal, determine a maximum amplitude associated with each of a plurality of the sensed event signals, identify a greatest maximum amplitude from the determined maximum amplitudes and determine at least one tachyarrhythmia metric based on at least the identified greatest maximum amplitude. The instructions further cause the device to determine the at least one tachyarrhythmia metric does not meet true tachyarrhythmia evidence criteria and, in response to the at least one tachyarrhythmia metric not meeting true tachyarrhythmia evidence criteria, determine that suspected noise criteria are met based on the determined maximum amplitudes. The instructions may cause the device to determine that a tachyarrhythmia detection criterion is met based on the sensed event signals and, in response to determining that suspected noise criteria are met, withhold a tachyarrhythmia detection when the tachyarrhythmia detection criterion is determined to be met.

This summary is intended to provide an overview of the subject matter described in this disclosure. It is not intended to provide an exclusive or exhaustive explanation of the apparatus and methods described in detail within the accompanying drawings and description below. Further details of one or more examples are set forth in the accompanying drawings and the description below.

DETAILED DESCRIPTION

Figure 1A:
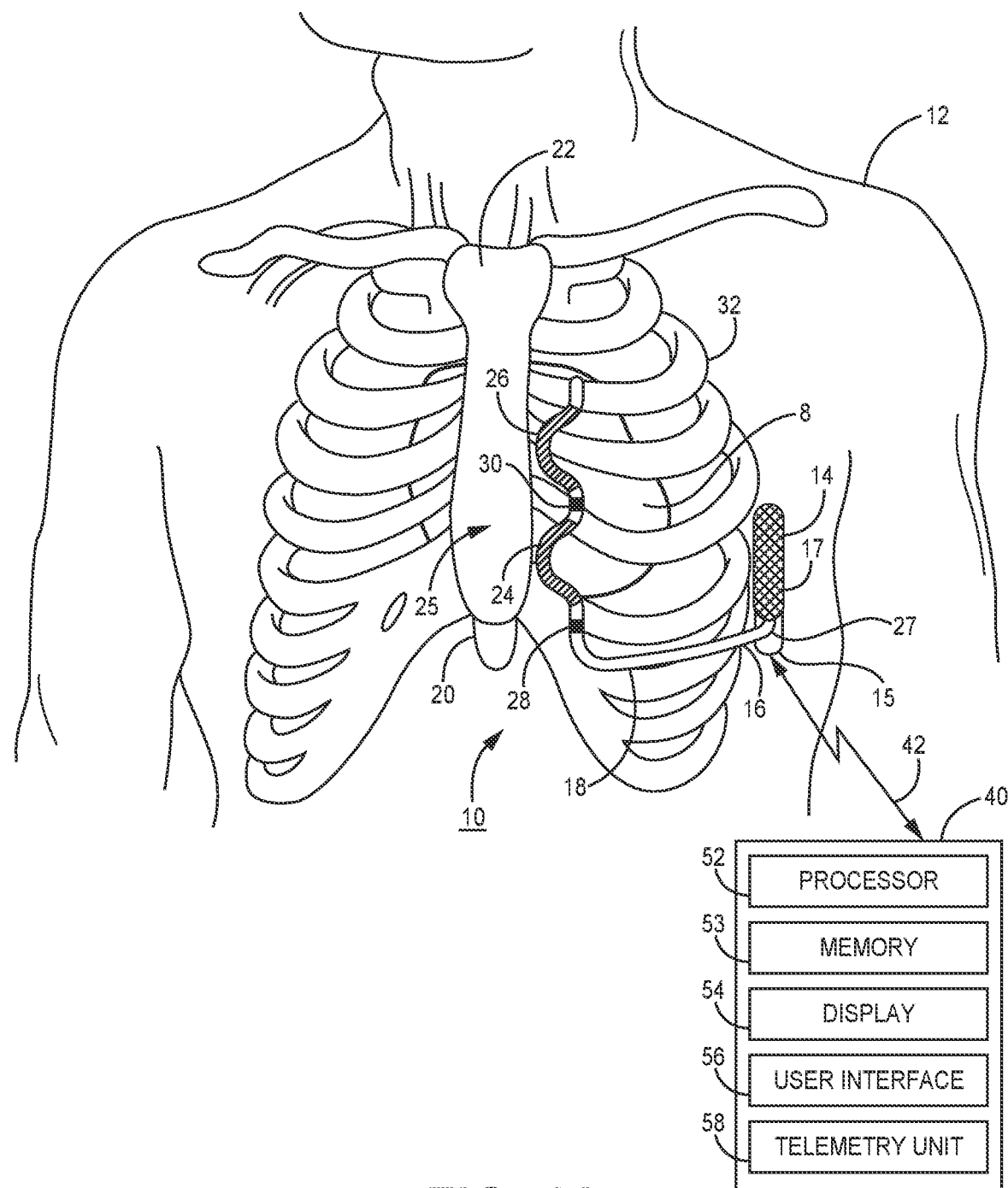
FIGS. 1A and 1B are conceptual diagrams of an extra-cardiovascular ICD system configured to sense cardiac electrical events and deliver cardiac electrical stimulation therapies according to one example.

In general, this disclosure describes a medical device and techniques for determining the presence of noise in an electrical signal sensed by the medical device, such as a cardiac electrical signal. In some examples, the medical device may be configured to sense cardiac electrical events attendant to myocardial depolarizations, e.g., atrial P-waves attendant to atrial myocardial depolarizations and/or ventricular R-waves attendant to ventricular myocardial depolarizations, from the cardiac electrical signal. The medical device may determine the heart rate or rhythm and a need for therapy delivery based on the sensed cardiac electrical event signals. For example, atrial or ventricular tachyarrhythmia may be detected by the medical device based on sensed cardiac electrical event signals. In some examples, the medical device may be configured to sense R-waves attendant to ventricular depolarizations from a cardiac electrical signal for use in controlling ventricular pacing and detecting ventricular tachyarrhythmias. A ventricular tachyarrhythmia may be detected in response to sensing a threshold number of R-waves occurring at a time interval from a preceding R-wave that is less than a tachyarrhythmia detection interval.

Non-cardiac electrical noise present in the cardiac signal, e.g., electromagnetic interference (EMI) or skeletal muscle myopotential signals, may be oversensed as R-waves, resulting in false, short RRIs being determined as ventricular tachyarrhythmia intervals. In some instances, variability in the R-wave signal strength due to patient motion or other factors may result in oversensing of non-cardiac noise, leading to relatively short RRIs being counted toward tachyarrhythmia detection when the underlying rhythm may actually be a normal sinus rhythm. False tachyarrhythmia detection may lead to a CV/DF shock or other tachyarrhythmia therapy delivered by the medical device, such as anti-tachyarrhythmia pacing (ATP), when a therapy may not be needed.

In some examples, the medical device performing the techniques disclosed herein may be included in an extra-cardiovascular ICD system. As used herein, the term "extra-cardiovascular" refers to a position outside the heart and/or blood vessels and/or pericardium surrounding the heart of a patient. Implantable electrodes carried by extra-cardiovascular leads may be positioned extra-thoracically (outside the ribcage and sternum) or intra-thoracically (beneath the ribcage or sternum) but generally not in intimate contact with myocardial tissue. The medical device may be coupled to a lead in an "extra-cardiac" location that positions electrodes within a blood vessel(s) not surrounding the heart. For example, a medical lead may be advanced along a venous pathway to position electrodes within the internal thoracic vein (ITV), an intercostal vein, the superior epigastric vein, or the azygos, hemiazygos, or accessory hemiazygos veins, as examples.

Patient positional changes or patient physical activity as well as other factors may lead to variation in the cardiac event signal amplitudes, e.g., P-wave amplitudes, R-wave amplitudes and T-wave amplitudes, in the signal sensed from an extra-cardiovascular or extra-cardiac location. Furthermore, the presence and amplitude of non-cardiac noise in a cardiac electrical signal may be highly variable. Cardiac signals sensed via extra-cardiovascular or extra-cardiac electrodes may be more susceptible to signal amplitude variability and noise contamination, e.g., due to myopotentials or environmental EMI, than cardiac signals sensed using transvenous intracardiac electrodes or epicardial electrodes. However, the techniques disclosed herein for determining noise corruption of a cardiac electrical signal may be implemented in conjunction with a variety of electrode configurations used for sensing cardiac electrical signals.

The medical device and techniques disclosed herein provide a method for determining the presence of noise in a cardiac electrical signal and withholding detection of a tachyarrhythmia when noise is determined to be present. The illustrative examples presented herein involve sensing cardiac electrical signals for the detection of ventricular tachyarrhythmia. The disclosed techniques, however, may be implemented in a medical device configured to sense atrial and/or ventricular cardiac events for detecting a variety of cardiac rhythms, such as bradycardia, tachycardia, fibrillation, etc. For example, a cardiac device using the disclosed techniques may be configured to sense P-waves, e.g., for detecting (and optionally treating) atrial tachyarrhythmia. In this case, the medical device may count PP intervals occurring between consecutively sensed atrial P-waves which are less than an atrial tachyarrhythmia detection interval. Cardiac electrical signals, which may be sensed from within or outside an atrial chamber, may be analyzed for determining noise corruption of the cardiac electrical signal using the techniques disclosed herein. An atrial tachyarrhythmia episode may be rejected or withheld based on a determination of noise corruption.

More generally, the disclosed techniques may be adapted for use in any device that is configured to determine a heart rate from sensed cardiac electrical signals, such as fitness trackers, watches, or other heart rate monitors. When the cardiac electrical signal is corrupted by non-cardiac noise, the determined heart rate may be incorrect, e.g., overestimated, due to the non-cardiac noise signals being falsely sensed as cardiac events.

Figure 1B:
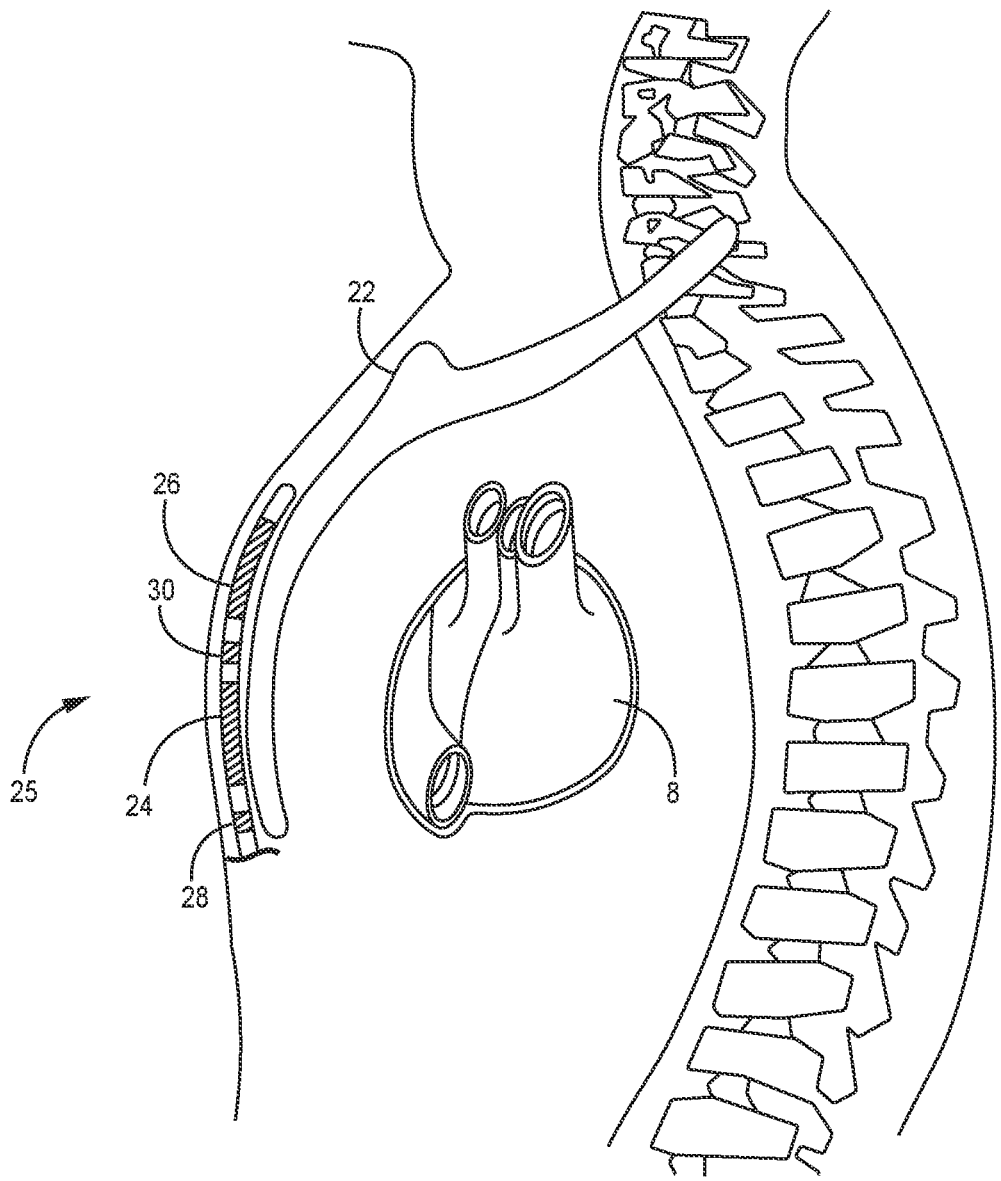

FIGS. 1A and 1B are conceptual diagrams of an ICD system 10 configured to sense cardiac electrical events and deliver cardiac electrical stimulation therapies according to one example. FIG. 1A is a front view of ICD system 10 implanted within patient 12. FIG. 1B is a side view of ICD system 10 implanted within patient 12. ICD system 10 includes an ICD 14 connected to an extra-cardiovascular electrical stimulation and sensing lead 16. FIGS. 1A and 1B are described in the context of an ICD system 10 capable of providing high voltage CV/DF shocks, and in some examples cardiac pacing pulses, in response to detecting a cardiac tachyarrhythmia.

ICD 14 includes a housing 15 that forms a hermetic seal that protects internal components of ICD 14. The housing 15 of ICD 14 may be formed of a conductive material, such as titanium or titanium alloy. The housing 15 may function as an electrode (sometimes referred to as a "can" electrode). Housing 15 may be used as an active can electrode for use in delivering CV/DF shocks or other high voltage pulses delivered using a high voltage therapy circuit. In other examples, housing 15 may be available for use in delivering unipolar, low voltage cardiac pacing pulses and/or for sensing cardiac electrical signals in combination with electrodes carried by lead 16. In other instances, the housing 15 of ICD 14 may include a plurality of electrodes on an outer portion of the housing. The outer portion(s) of the housing 15 functioning as an electrode(s) may be coated with a material, such as titanium nitride, e.g., for reducing post-stimulation polarization artifact.

ICD 14 includes a connector assembly 17 (also referred to as a connector block or header) that includes electrical feedthroughs crossing housing 15 to provide electrical connections between conductors extending within the lead body 18 of lead 16 and electronic components included within the housing 15 of ICD 14. As will be described in further detail herein, housing 15 may house one or more processors, memories, transceivers, cardiac electrical signal sensing circuitry, therapy delivery circuitry, power sources and other components for sensing cardiac electrical signals, detecting a heart rhythm, and controlling and delivering electrical stimulation pulses to treat an abnormal heart rhythm.

Elongated lead body 18 has a proximal end 27 that includes a lead connector (not shown) configured to be connected to ICD connector assembly 17 and a distal portion 25 that includes one or more electrodes. In the example illustrated in FIGS. 1A and 1B, the distal portion 25 of lead body 18 includes defibrillation electrodes 24 and 26 and pace/sense electrodes 28 and 30. In some cases, defibrillation electrodes 24 and 26 may together form a defibrillation electrode in that they may be configured to be activated concurrently. Alternatively, defibrillation electrodes 24 and 26 may form separate defibrillation electrodes in which case each of the electrodes 24 and 26 may be activated independently.

Electrodes 24 and 26 (and in some examples housing 15) are referred to herein as defibrillation electrodes because they are utilized, individually or collectively, for delivering high voltage stimulation therapy (e.g., cardioversion or defibrillation shocks). Electrodes 24 and 26 may be elongated coil electrodes and generally have a relatively high surface area for delivering high voltage electrical stimulation pulses compared to pacing and sensing electrodes 28 and 30. However, electrodes 24 and 26 and housing 15 may also be utilized to provide pacing functionality, sensing functionality or both pacing and sensing functionality in addition to or instead of high voltage stimulation therapy. In this sense, the use of the term "defibrillation electrode" herein should not be considered as limiting the electrodes 24 and 26 for use in only high voltage cardioversion/defibrillation shock therapy applications. For example, either of electrodes 24 and 26 may be used as a sensing electrode in a sensing vector for sensing cardiac electrical signals and determining a need for an electrical stimulation therapy.

Electrodes 28 and 30 are relatively smaller surface area electrodes which are available for use in sensing electrode vectors for sensing cardiac electrical signals and may be used for delivering relatively low voltage pacing pulses in some configurations. Electrodes 28 and 30 are referred to as pace/sense electrodes because they are generally configured for use in low voltage applications, e.g., used as either a cathode or anode for delivery of pacing pulses and/or sensing of cardiac electrical signals, as opposed to delivering high voltage CV/DF shocks. In some instances, electrodes 28 and 30 may provide only pacing functionality, only sensing functionality or both.

ICD 14 may sense cardiac electrical signals corresponding to electrical activity of heart 8 via a combination of sensing electrode vectors that include combinations of electrodes 24, 26, 28 and/or 30. In some examples, housing 15 of ICD 14 is used in combination with one or more of electrodes 24, 26, 28 and/or 30 in a sensing electrode vector. Various sensing electrode vectors utilizing combinations of electrodes 24, 26, 28, and 30 and housing 15 may be selected sensing at least one cardiac electrical signal and sensing cardiac events from the cardiac electrical signal. In some example, two or more sensing electrode vectors may be selected from the available electrodes for sensing two or more cardiac electrical signals using the respective sensing electrode vectors.

In the example illustrated in FIGS. 1A and 1B, electrode 28 is located proximal to defibrillation electrode 24, and electrode 30 is located between defibrillation electrodes 24 and 26. One, two or more pace/sense electrodes may be carried by lead body 18. For instance, a third pace/sense electrode may be located distal to defibrillation electrode 26 in some examples. Electrodes 28 and 30 are illustrated as ring electrodes; however, electrodes 28 and 30 may comprise any of a number of different types of electrodes, including ring electrodes, short coil electrodes, hemispherical electrodes, directional electrodes, segmented electrodes, or the like. Electrodes 28 and 30 may be positioned at other locations along lead body 18 and are not limited to the positions shown. In other examples, lead 16 may include fewer or more pace/sense electrodes and/or defibrillation electrodes than the example shown here.

In the example shown, lead 16 extends subcutaneously or submuscularly over the ribcage 32 medially from the connector assembly 27 of ICD 14 toward a center of the torso of patient 12, e.g., toward xiphoid process 20 of patient 12. At a location near xiphoid process 20, lead 16 bends or turns and extends superiorly, subcutaneously or submuscularly, over the ribcage and/or sternum, substantially parallel to sternum 22. Although illustrated in FIG. 1A as being offset laterally from and extending substantially parallel to sternum 22, the distal portion 25 of lead 16 may be implanted at other locations, such as over sternum 22, offset to the right or left of sternum 22, angled laterally from sternum 22 toward the left or the right, or the like. Alternatively, lead 16 may be placed along other subcutaneous or submuscular paths. The path of extra-cardiovascular lead 16 may depend on the location of ICD 14, the arrangement and position of electrodes carried by the lead body 18, and/or other factors. The techniques disclosed herein are not limited to a particular path of lead 16 or final locations of electrodes 24, 26, 28 and 30 carried by a lead for sensing cardiac electrical signals.

Electrical conductors (not illustrated) extend through one or more lumens of the elongated lead body 18 of lead 16 from the lead connector at the proximal lead end 27 to electrodes 24, 26, 28, and 30 located along the distal portion 25 of the lead body 18. The elongated electrical conductors contained within the lead body 18, which may be separate respective insulated conductors within the lead body 18, are each electrically coupled with respective defibrillation electrodes 24 and 26 and pace/sense electrodes 28 and 30. The respective conductors electrically couple the electrodes 24, 26, 28, and 30 to circuitry, such as a therapy delivery circuit and/or a sensing circuit, of ICD 14 via connections in the connector assembly 17, including associated electrical feedthroughs crossing housing 15. The electrical conductors transmit therapy from a therapy delivery circuit within ICD 14 to one or more of defibrillation electrodes 24 and 26 and/or pace/sense electrodes 28 and 30 and transmit sensed electrical signals produced by the patient's heart 8 from one or more of defibrillation electrodes 24 and 26 and/or pace/sense electrodes 28 and 30 to the sensing circuit within ICD 14.

The lead body 18 of lead 16 may be formed from a non-conductive material, including silicone, polyurethane, fluoropolymers, mixtures thereof, and/or other appropriate materials, and shaped to form one or more lumens within which the one or more conductors extend. Lead body 18 may be tubular or cylindrical in shape. In other examples, the distal portion 25 (or all of) the elongated lead body 18 may have a flat, ribbon or paddle shape. Lead body 18 may be formed having a preformed distal portion 25 that is generally straight, curving, bending, serpentine, undulating or zig-zagging.

In the example shown, lead body 18 includes a curving distal portion 25 having two "C" shaped curves, which together may resemble the Greek letter epsilon, "ε." Defibrillation electrodes 24 and 26 are each carried by one of the two respective C-shaped portions of the lead body distal portion 25. The two C-shaped curves are seen to extend or curve in the same direction away from a central axis of lead body 18, along which pace/sense electrodes 28 and 30 are positioned. Pace/sense electrodes 28 and 30 may, in some instances, be approximately aligned with the central axis of the straight, proximal portion of lead body 18 such that mid-points of defibrillation electrodes 24 and 26 are laterally offset from pace/sense electrodes 28 and 30.

Other examples of extra-cardiovascular leads including one or more defibrillation electrodes and one or more pacing and sensing electrodes carried by curving, serpentine, undulating or zig-zagging distal portion of the lead body 18 that may be implemented with the techniques described herein are generally disclosed in pending U.S. Pat. Publication No. 2016/0158567 (Marshall, et al.), incorporated herein by reference in its entirety. The techniques disclosed herein are not limited to any particular lead body design, however. In other examples, lead body 18 is a flexible elongated lead body without any pre-formed shape, bends or curves.

ICD 14 analyzes the cardiac electrical signals received from one or more sensing electrode vectors to monitor for abnormal rhythms, such as bradycardia, ventricular tachycardia (VT) or ventricular fibrillation (VF). ICD 14 may analyze the heart rate and morphology of the cardiac electrical signals to monitor for tachyarrhythmia in accordance with any of a number of tachyarrhythmia detection techniques. Example techniques for detecting a tachyarrhythmia are described in conjunction with the flow charts and diagrams presented herein.

ICD 14 generates and delivers electrical stimulation therapy in response to detecting a tachyarrhythmia (e.g., VT or VF) using a therapy delivery electrode vector which may be selected from any of the available electrodes 24, 26, 28 30 and/or housing 15. ICD 14 may deliver ATP in response to VT detection and in some cases may deliver ATP prior to a CV/DF shock or during high voltage capacitor charging in an attempt to avert the need for delivering a CV/DF shock. If ATP does not successfully terminate VT or when VF is detected, ICD 14 may deliver one or more CV/DF shocks via one or both of defibrillation electrodes 24 and 26 and/or housing 15. ICD 14 may deliver the CV/DF shocks using electrodes 24 and 26 individually or together as a cathode (or anode) and with the housing 15 as an anode (or cathode). ICD 14 may generate and deliver other types of electrical stimulation pulses such as post-shock pacing pulses, asystole pacing pulses, or bradycardia pacing pulses using a pacing electrode vector that includes one or more of the electrodes 24, 26, 28, and 30 and the housing 15 of ICD 14.

ICD 14 is shown implanted subcutaneously on the left side of patient 12 along the ribcage 32. ICD 14 may, in some instances, be implanted between the left posterior axillary line and the left anterior axillary line of patient 12. ICD 14 may, however, be implanted at other subcutaneous or submuscular locations in patient 12. For example, ICD 14 may be implanted in a subcutaneous pocket in the pectoral region. In this case, lead 16 may extend subcutaneously or submuscularly from ICD 14 toward the manubrium of sternum 22 and bend or turn and extend inferiorly from the manubrium to the desired location subcutaneously or submuscularly. In yet another example, ICD 14 may be placed abdominally. Lead 16 may be implanted in other extra-cardiovascular or extra-cardiac locations as well. For instance, as described with respect to FIGS. 2A-2C, the distal portion 25 of lead 16 may be implanted underneath the sternum/ribcage in the substernal space. FIGS. 1A and 1B are illustrative in nature and should not be considered limiting of the practice of the techniques disclosed herein.

An external device 40 is shown in telemetric communication with ICD 14 by a communication link 42. External device 40 may include a processor 52, memory 53, display 54, user interface 56 and telemetry unit 58. Processor 52 controls external device operations and processes data and signals received from ICD 14. Display 54, which may include a graphical user interface, displays data and other information to a user for reviewing ICD operation and programmed parameters as well as cardiac electrical signals retrieved from ICD 14.

User interface 56 may include a mouse, touch screen, key pad or the like to enable a user to interact with external device 40 to initiate a telemetry session with ICD 14 for retrieving data from and/or transmitting data to ICD 14, including programmable parameters for controlling cardiac event sensing and therapy delivery. Telemetry unit 58 includes a transceiver and antenna configured for bidirectional communication with a telemetry circuit included in ICD 14 and is configured to operate in conjunction with processor 52 for sending and receiving data relating to ICD functions via communication link 42.

Communication link 42 may be established between ICD 14 and external device 40 using a radio frequency (RF) link such as BLUETOOTH®, Wi-Fi, or Medical Implant Communication Service (MICS) or other RF or communication frequency bandwidth or communication protocols. Data stored or acquired by ICD 14, including physiological signals or associated data derived therefrom, results of device diagnostics, and histories of detected rhythm episodes and delivered therapies, may be retrieved from ICD 14 by external device 40 following an interrogation command.

External device 40 may be embodied as a programmer used in a hospital, clinic or physician's office to retrieve data from ICD 14 and to program operating parameters and algorithms in ICD 14 for controlling ICD functions. External device 40 may alternatively be embodied as a home monitor or hand held device. External device 40 may be used to program cardiac signal sensing parameters, cardiac rhythm detection parameters and therapy control parameters used by ICD 14. At least some control parameters used in detecting noise according to techniques disclosed herein may be programmed into ICD 14 using external device 40 in some examples.

Figure 2A:
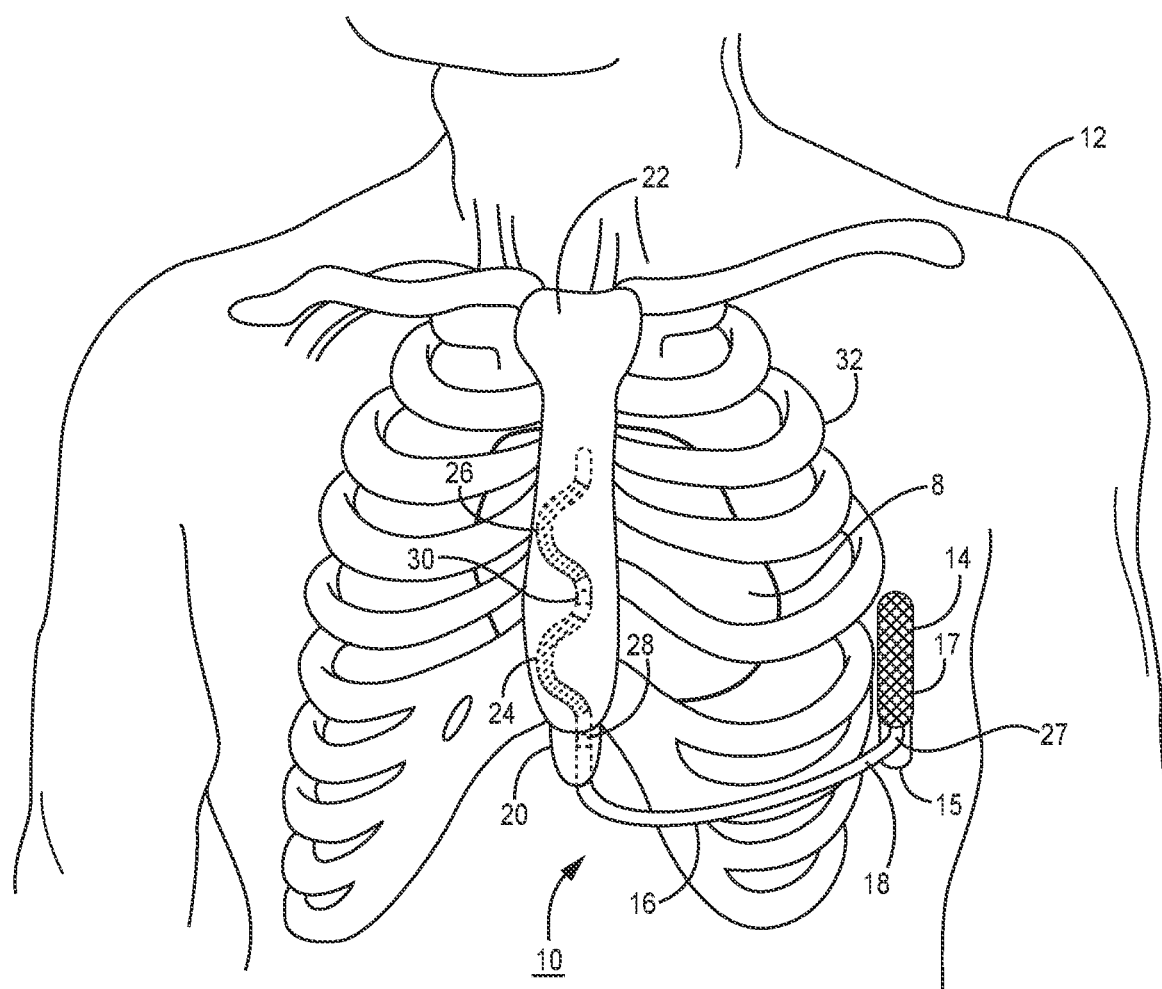
FIGS. 2A-2C are conceptual diagrams of a patient implanted with an extra-cardiovascular ICD system in a different implant configuration than the arrangement shown in FIGS. 1A-1B.
Figure 2B:
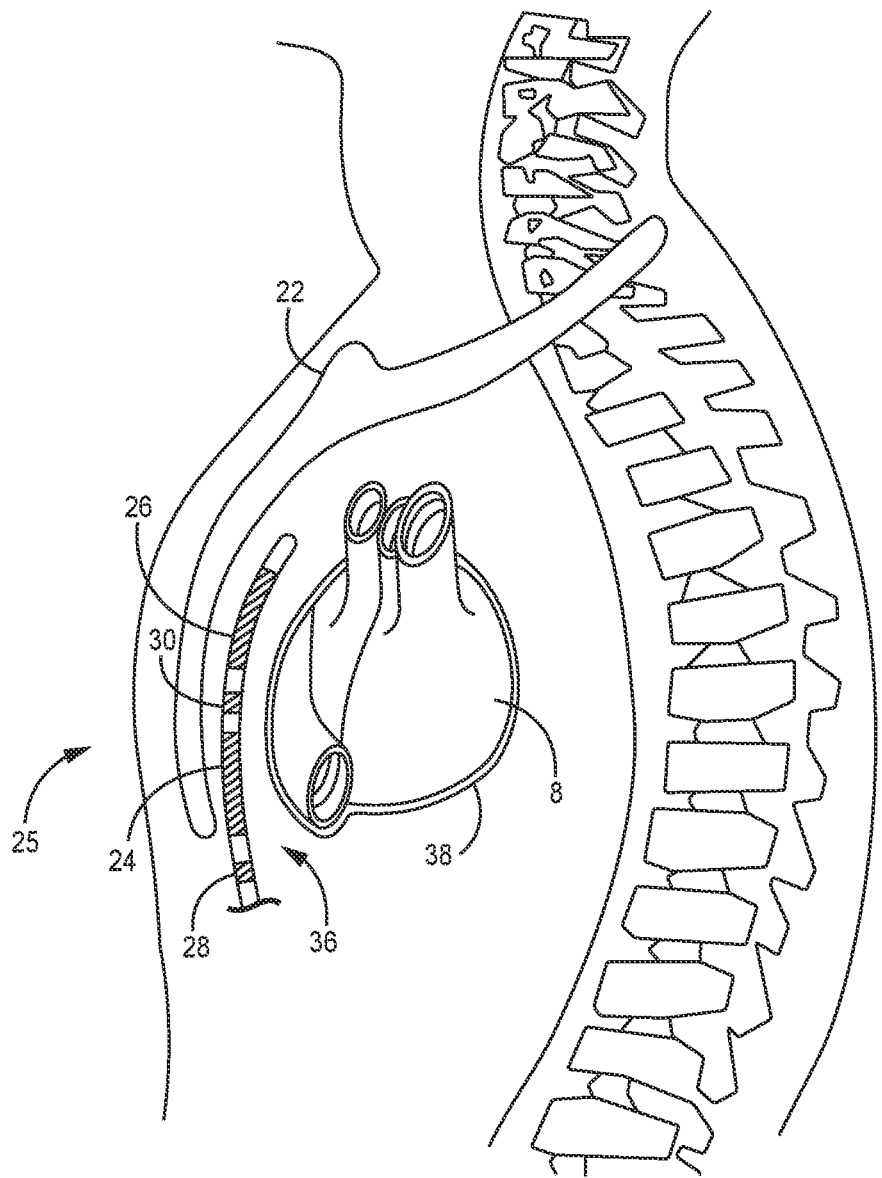
Figure 2C:
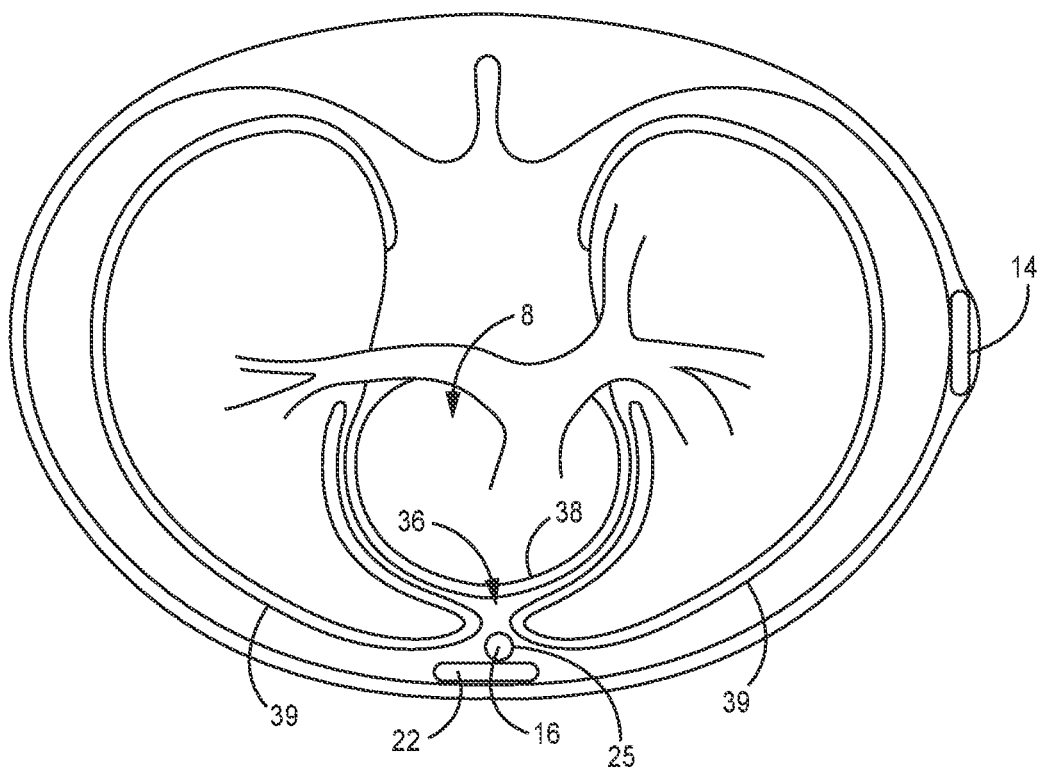

FIGS. 2A-2C are conceptual diagrams of patient 12 implanted with extra-cardiovascular ICD system 10 in a different implant configuration than the arrangement shown in FIGS. 1A-1B. FIG. 2A is a front view of patient 12 implanted with ICD system 10. FIG. 2B is a side view of patient 12 implanted with ICD system 10. FIG. 2C is a transverse view of patient 12 implanted with ICD system 10. In this arrangement, extra-cardiovascular lead 16 of system 10 is implanted at least partially underneath sternum 22 of patient 12. Lead 16 extends subcutaneously or submuscularly from ICD 14 toward xiphoid process 20 and at a location near xiphoid process 20 bends or turns and extends superiorly within anterior mediastinum 36 in a substernal position.

Anterior mediastinum 36 may be viewed as being bounded laterally by pleurae 39, posteriorly by pericardium 38, and anteriorly by sternum 22 (see FIG. 2C) and may include loose connective tissue (such as areolar tissue), some lymph vessels, lymph glands, substernal musculature (e.g., transverse thoracic muscle), branches of the internal thoracic artery, and the internal thoracic vein. The distal portion 25 of lead 16 may extend along the posterior side of sternum 22 substantially within the anterior mediastinum 36. A lead implanted such that the distal portion 25 is substantially within anterior mediastinum 36, may be referred to as a "substernal lead."

In the example illustrated in FIGS. 2A-2C, lead 16 is located substantially centered under sternum 22. In other instances, however, lead 16 may be implanted such that it is offset laterally from the center of sternum 22. In some instances, lead 16 may extend laterally such that distal portion 25 of lead 16 is underneath/below the ribcage 32 in addition to or instead of sternum 22. In other examples, the distal portion 25 of lead 16 may be implanted in other extra-cardiovascular, intra-thoracic locations, including the pleural cavity or around the perimeter of and adjacent to the pericardium 38 of heart 8. For example, the distal portion 25 of lead 16 may be advanced to a supra-diaphragmatic position, which may be within the thoracic cavity or outside the thorax in various examples. As described above, lead 16 may alternatively be advanced within a vein to position electrodes for delivering electrical stimulation pulses to heart 8 from an intravenous location.

In the various example implant locations of lead 16 and electrodes 24, 26, 28 and 30, cardiac signals sensed by ICD 14 may be contaminated by skeletal muscle myopotentials, environmental EMI or other non-cardiac electrical noise.

Some noise signals may be oversensed as cardiac event signals, e.g., R-waves, resulting in a false heart rate being determined. A false tachyarrhythmia detection may be made, or bradycardia pacing may be withheld when it is actually needed. Withholding a tachyarrhythmia detection when noise is suspected but the underlying rhythm is a true tachyarrhythmia may result in a therapy being withheld when it is actually needed. Accordingly, the techniques disclosed herein provide improvements in non-cardiac noise detection by applying criteria for detecting suspected noise signals and verifying that evidence of a true tachyarrhythmia morphology and/or true cardiac event intervals is not present before determining noise corruption of the cardiac electrical signal and withholding a tachyarrhythmia detection due to noise when other tachyarrhythmia detection criteria are met. When noise is suspected but evidence of a true tachyarrhythmia is determined from the cardiac electrical signal, the suspected noise does not cause withholding of a tachyarrhythmia detection by ICD 10 when other tachyarrhythmia detection criteria are met.

Figure 3:
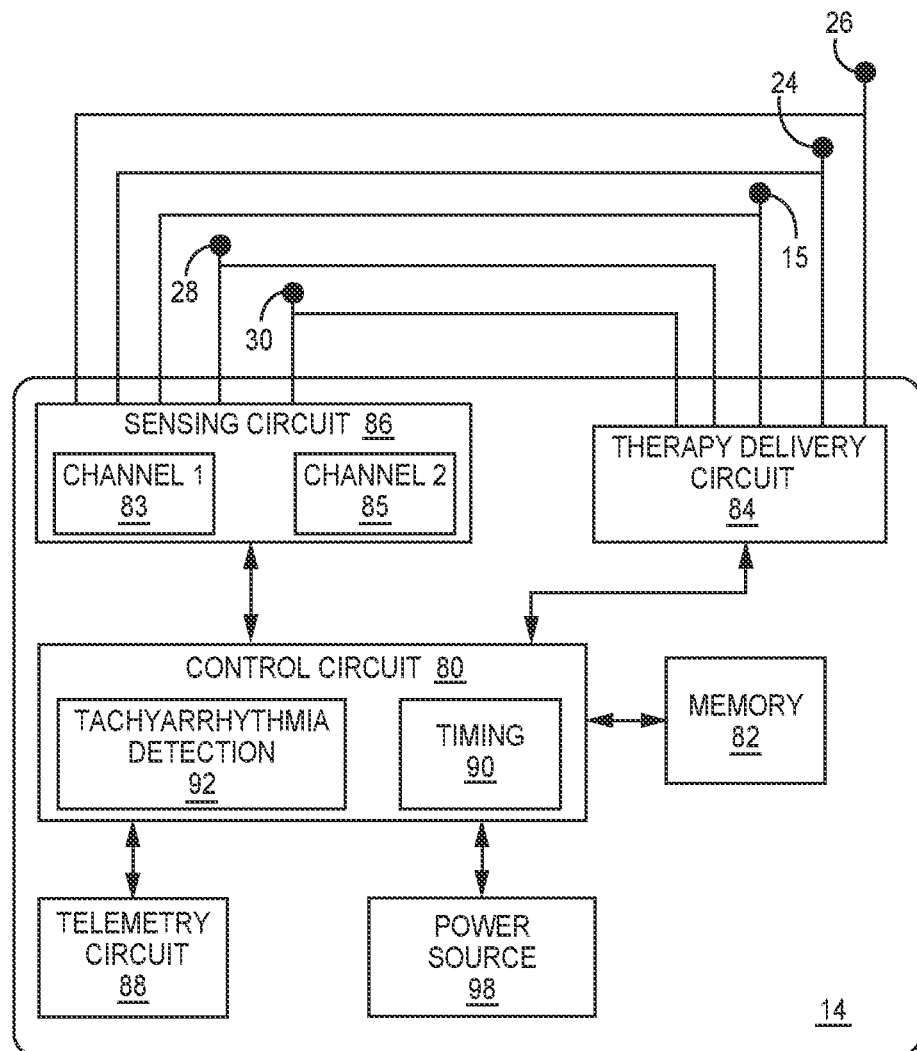
FIG. 3 is a conceptual diagram of an ICD according to one example.

FIG. 3 is a conceptual diagram of ICD 14 according to one example. The electronic circuitry enclosed within housing 15 (shown schematically as an electrode in FIG. 3) includes software, firmware and hardware that cooperatively monitor cardiac electrical signals, determine when an electrical stimulation therapy is necessary, and deliver therapy as needed according to programmed therapy delivery algorithms and control parameters. ICD 14 may be coupled to an extra-cardiovascular lead, such as lead 16 carrying extra-cardiovascular electrodes 24, 26, 28, and 30, for delivering electrical stimulation pulses to the patient's heart and for sensing cardiac electrical signals.

ICD 14 includes a control circuit 80, memory 82, therapy delivery circuit 84, cardiac electrical signal sensing circuit 86, and telemetry circuit 88. A power source 98 provides power to the circuitry of ICD 14, including each of the components 80, 82, 84, 86, and 88 as needed. Power source 98 may include one or more energy storage devices, such as one or more rechargeable or non-rechargeable batteries. The connections between power source 98 and each of the other components 80, 82, 84, 86 and 88 are to be understood from the general block diagram of FIG. 3, but are not shown for the sake of clarity. For example, power source 98 may be coupled to one or more charging circuits included in therapy delivery circuit 84 for charging holding capacitors included in therapy delivery circuit 84 that are discharged at appropriate times under the control of control circuit 80 for producing electrical pulses according to a therapy protocol. Power source 98 is also coupled to components of cardiac electrical signal sensing circuit 86, such as sense amplifiers, analog-to-digital converters, switching circuitry, etc. as needed.

The circuits shown in FIG. 3 represent functionality included in ICD 14 and may include any discrete and/or integrated electronic circuit components that implement analog and/or digital circuits capable of producing the functions attributed to ICD 14 herein. Functionality associated with one or more circuits may be performed by separate hardware, firmware or software components, or integrated within common hardware, firmware or software components. For example, cardiac event sensing and detection of noise for rejecting sensed events or withholding detection of a tachyarrhythmia based on cardiac event intervals may be performed cooperatively by sensing circuit 86 and control circuit 80 and may include operations implemented in a processor or other signal processing circuitry included in control circuit 80 executing instructions stored in memory 82 and control signals such as blanking and timing intervals and sensing threshold amplitude signals sent from control circuit 80 to sensing circuit 86.

The various circuits of ICD 14 may include an application specific integrated circuit (ASIC), an electronic circuit, a processor (shared, dedicated, or group) and memory that execute one or more software or firmware programs, a combinational logic circuit, state machine, or other suitable components or combinations of components that provide the described functionality. The particular form of software, hardware and/or firmware employed to implement the functionality disclosed herein will be determined primarily by the particular system architecture employed in the ICD and by the particular detection and therapy delivery methodologies employed by the ICD. Providing software, hardware, and/or firmware to accomplish the described functionality in the context of any modern medical device system, given the disclosure herein, is within the abilities of one of skill in the art.

Memory 82 may include any volatile, non-volatile, magnetic, or electrical non-transitory computer readable storage media, such as random access memory (RAM), read-only memory (ROM), non-volatile RAM (NVRAM), electrically-erasable programmable ROM (EEPROM), flash memory, or any other memory device. Furthermore, memory 82 may include non-transitory computer readable media storing instructions that, when executed by one or more processing circuits, cause control circuit 80 and/or other ICD components to perform various functions attributed to ICD 14 or those ICD components. The non-transitory computer-readable media storing the instructions may include any of the media listed above.

Control circuit 80 communicates, e.g., via a data bus, with therapy delivery circuit 84 and sensing circuit 86 for sensing cardiac electrical activity, detecting cardiac rhythms, and controlling delivery of cardiac electrical stimulation therapies in response to sensed cardiac signals. Therapy delivery circuit 84 and sensing circuit 86 are electrically coupled to electrodes 24, 26, 28, 30 carried by lead 16 and the housing 15, which may function as a common or ground electrode or as an active can electrode for delivering CV/DF shock pulses or cardiac pacing pulses.

Cardiac electrical signal sensing circuit 86 (also referred to herein as "sensing circuit" 86) may be selectively coupled to electrodes 28, 30 and/or housing 15 in order to monitor electrical activity of the patient's heart. Sensing circuit 86 may additionally be selectively coupled to defibrillation electrodes 24 and/or 26 for use in a sensing electrode vector together or in combination with one or more of electrodes 28, 30 and/or housing 15. Sensing circuit 86 may be enabled to selectively receive cardiac electrical signals from one or more sensing electrode vectors from the available electrodes 24, 26, 28, 30, and housing 15. In some examples, at least two cardiac electrical signals from two different sensing electrode vectors may be received simultaneously by sensing circuit 86. Sensing circuit 86 may monitor one or both of the cardiac electrical signals simultaneously for sensing cardiac electrical events and/or producing digitized cardiac signal waveforms for analysis by control circuit 80. For example, sensing circuit 86 may include switching circuitry for selecting which of electrodes 24, 26, 28, 30, and housing 15 are coupled to a first sensing channel 83 and which electrodes are coupled to a second sensing channel 85 of sensing circuit 86.

Each sensing channel 83 and 85 may be configured to amplify, filter and digitize the cardiac electrical signal received from selected electrodes coupled to the respective sensing channel to improve the signal quality for detecting cardiac electrical events, such as R-waves or performing other signal analysis. The cardiac event detection circuitry within sensing circuit 86 may include one or more sense amplifiers, filters, rectifiers, threshold detectors, comparators, analog-to-digital converters (ADCs), timers or other analog or digital components as described further in conjunction with FIG. 4. A cardiac event sensing threshold may be automatically adjusted by sensing circuit 86 under the control of control circuit 80, based on timing intervals and sensing threshold values determined by control circuit 80, stored in memory 82, and/or controlled by hardware, firmware and/or software of control circuit 80 and/or sensing circuit 86.

Upon detecting a cardiac event based on a sensing threshold crossing, first sensing channel 83 may produce a sensed event signal, such as an R-wave sensed event signal, that is passed to control circuit 80. The R-wave sensed event signals may be used by control circuit 80 for determining RRIs for detecting tachyarrhythmia and determining a need for therapy. An RRI is the time interval between two consecutively sensed R-waves and may be determined between consecutive R-wave sensed event signals received by control circuit 80 from sensing circuit 86. For example, control circuit 80 may include a timing circuit 90 for determining RRIs between consecutive R-wave sensed event signals received from sensing circuit 86 and for controlling various timers and/or counters used to control the timing of therapy delivery by therapy delivery circuit 84. Timing circuit 90 may additionally set time windows such as morphology template windows, morphology analysis windows or perform other timing related functions of ICD 14 including synchronizing cardioversion shocks or other therapies delivered by therapy delivery circuit 84 with sensed cardiac events.

The R-wave sensed event signals may be used by control circuit 80 to trigger storage of a time segment of a cardiac electrical signal for processing and analysis for detecting noise in the cardiac electrical signal as described below. In some examples, sensing circuit 86 senses at least one cardiac electrical signal received by a sensing electrode vector selected from the available electrodes, e.g., electrodes 24, 26, 28, 30 and housing 15, for detecting R-waves and buffering multiple cardiac electrical signal segments, where each cardiac electrical signal segment corresponds to a detected R-wave, for processing and analysis for detecting noise. A single cardiac electrical signal sensed by first sensing channel 83 may be used for both R-wave sensing and analysis of cardiac electrical signal segments for noise detection and true, underlying tachyarrhythmia evidence determination. In other examples, R-waves are detected from the first cardiac electrical signal sensed by the first sensing channel 83 and segments of a second cardiac electrical signal sensed by the second sensing channel 85 may be buffered, with each segment corresponding to an R-wave sensed from the first cardiac electrical signal. Analysis for determining noise corruption may be performed on the second cardiac electrical signal segments. The second cardiac electrical signal may be received via a sensing electrode pair coupled to the second sensing channel 85 different than the sensing electrode pair coupled to the first sensing channel 83 for sensing than the first cardiac electrical signal and/or may be received by the same sensing electrode pair but processed differently, e.g., filtered differently, by the second sensing channel 85 to produce a second cardiac electrical signal sensed by sensing circuit 86 different than the first cardiac electrical signal.

Memory 82 may be configured to store a predetermined number of cardiac electrical signal segments in a circulating buffer under the control of control circuit 80, e.g., at least one, two, three or other number of cardiac electrical signal segments. Each segment may be written to memory 82 over a time interval extending before and after an R-wave sensed event signal produced by the first sensing channel 83. Control circuit 80 may access stored cardiac electrical signal segments when confirmation of R-waves sensed by the first sensing channel 83 is required based on the detection of a predetermined number of tachyarrhythmia intervals, which may precede tachyarrhythmia detection. In some examples, R-waves sensed by the first sensing channel 83 may be rejected when a cardiac electrical signal sensed by the second sensing channel 85 is determined to be noise corrupted. In other examples, R-waves sensed by the first sensing channel 83 may be used by control circuit 80 to determine RRIs that may be counted as tachyarrhythmia intervals, but when a tachyarrhythmia detection criterion is satisfied based on the RRIs, control circuit 80 may withhold tachyarrhythmia detection if the second cardiac electrical signal is determined to be noise corrupted. Methods for determining that noise is present in a cardiac electrical signal are described below.

Control circuit 80 is shown to include a tachyarrhythmia detector 92 configured to analyze signals received from sensing circuit 86 for detecting tachyarrhythmia. Tachyarrhythmia detector 92 may detect tachyarrhythmia based on R-wave sensed event signals meeting tachyarrhythmia criteria, such as a threshold number of sensed event signals occurring at a tachyarrhythmia interval. In some examples, a tachyarrhythmia detection based on the threshold number of sensed event signals each occurring at a tachyarrhythmia interval may be rejected based on non-cardiac noise being detected using the techniques disclosed herein. Tachyarrhythmia detector 92 may be implemented in control circuit 80 as hardware, software and/or firmware that processes and analyzes signals received from sensing circuit 86 for detecting VT and/or VF. In some examples, the timing of R-wave sensed event signals received from sensing circuit 86 is used by timing circuit 90 to determine RRIs between sensed event signals. These RRIs may also be referred to herein as "sensed event intervals." Tachyarrhythmia detector 92 may include comparators and counters for counting RRIs determined by timing circuit 90 that fall into various rate detection zones for determining a ventricular rate or performing other rate- or interval-based assessment of R-wave sensed event signals for detecting and discriminating VT and VF.

For example, tachyarrhythmia detector 92 may compare the RRIs determined by timing circuit 90 to one or more tachyarrhythmia detection interval zones, such as a tachycardia detection interval zone and a fibrillation detection interval zone. RRIs falling into a detection interval zone are counted by a respective VT interval counter or VF interval counter and in some cases in a combined VT/VF interval counter included in tachyarrhythmia detector 92. The VF detection interval threshold may be set to 300 to 350 milliseconds (ms), as examples. For instance, if the VF detection interval is set to 320 ms, RRIs that are less than 320 ms are counted by the VF interval counter. When VT detection is enabled, the VT detection interval may be programmed to be in the range of 350 to 420 ms, or 400 ms as an example. In order to detect VT or VF, the respective VT or VF interval counter is required to reach a threshold "number of intervals to detect" (NID).

As an example, the NID to detect VT may require that the VT interval counter reaches 32 VT intervals counted out of the most recent 32 consecutive RRIs. The NID required to detect VF may be programmed to 18 VF intervals out of the most recent 24 consecutive RRIs or 30 VF intervals out 40 consecutive RRIs, as examples. When a VT or VF interval counter reaches an NID threshold, a ventricular tachyarrhythmia may be detected by tachyarrhythmia detector 92. The NID may be programmable and range from as low as 12 to as high as 40, with no limitation intended. VT or VF intervals may be detected consecutively or non-consecutively out of the specified number of most recent RRIs. In some cases, a combined VT/VF interval counter may count both VT and VF intervals and detect a tachyarrhythmia episode based on the fastest intervals detected when a specified NID is reached.

Tachyarrhythmia detector 92 may be configured to perform other signal analysis for determining if other detection criteria are satisfied before detecting VT or VF, such as R-wave morphology criteria, onset criteria, and noise and oversensing rejection criteria. Examples of parameters that may be determined from cardiac electrical signals received from sensing circuit 86 for determining noise corruption that may cause withholding of a VT or VF detection are described below.

To support these additional analyses, sensing circuit 86 may pass a digitized electrocardiogram (ECG) signal to control circuit 80 for morphology analysis performed by tachyarrhythmia detector 92. A cardiac electrical signal from the selected sensing vector, e.g., from first sensing channel 83 and/or the second sensing channel 85, may be passed through a filter and amplifier, provided to a multiplexer and thereafter converted to a multi-bit digital signal by an analog-to-digital converter, all included in sensing circuit 86, for storage in memory 82. Memory 82 may include one or more circulating buffers to temporarily store digital cardiac electrical signal segments for analysis performed by control circuit 80. Control circuit 80 may be a microprocessor-based controller that employs digital signal analysis techniques to characterize the digitized signals stored in memory 82 to recognize and classify the patient's heart rhythm employing any of numerous signal processing methodologies for analyzing cardiac signals and cardiac event waveforms, e.g., R-waves. As described below, processing and analysis of digitized signals may include determining signal features or metrics for detecting noise present in the cardiac electrical signal(s). When noise is detected, a tachyarrhythmia detection based on RRIs may be withheld to inhibit a tachyarrhythmia therapy. Alternatively, a tachyarrhythmia therapy may be withheld in response to a tachyarrhythmia detection made when noise is also detected.

Therapy delivery circuit 84 includes charging circuitry, one or more charge storage devices such as one or more high voltage capacitors and/or low voltage capacitors, and switching circuitry that controls when the capacitor(s) are discharged across a selected pacing electrode vector or CV/DF shock vector. Charging of capacitors to a programmed pulse amplitude and discharging of the capacitors for a programmed pulse width may be performed by therapy delivery circuit 84 according to control signals received from control circuit 80. Control circuit 80 may include various timers or counters that control when cardiac pacing pulses are delivered. For example, timing circuit 90 may include programmable digital counters set by a microprocessor of the control circuit 80 for controlling the basic pacing time intervals associated with various pacing modes or ATP sequences delivered by ICD 14. The microprocessor of control circuit 80 may also set the amplitude, pulse width, polarity or other characteristics of the cardiac pacing pulses, which may be based on programmed values stored in memory 82.

In response to detecting VT or VF, control circuit 80 may schedule a therapy and control therapy delivery circuit 84 to generate and deliver the therapy, such as ATP and/or CV/DF therapy. Therapy can be generated by initiating charging of high voltage capacitors via a charging circuit, both included in therapy delivery circuit 84. Charging is controlled by control circuit 80 which monitors the voltage on the high voltage capacitors, which is passed to control circuit 80 via a charging control line. When the voltage reaches a predetermined value set by control circuit 80, a logic signal is generated on a capacitor full line and passed to therapy delivery circuit 84, terminating charging. A CV/DF pulse is delivered to the heart under the control of the timing circuit 90 by an output circuit of therapy delivery circuit 84 via a control bus. The output circuit may include an output capacitor through which the charged high voltage capacitor is discharged via switching circuitry, e.g., an H-bridge, which determines the electrodes used for delivering the cardioversion or defibrillation pulse and the pulse wave shape.

In some examples, the high voltage therapy circuit configured to deliver CV/DF shock pulses can be controlled by control circuit 80 to deliver pacing pulses, e.g., for delivering ATP, post shock pacing pulses or ventricular pacing pulses. In other examples, therapy delivery circuit 84 may include a low voltage therapy circuit for generating and delivering pacing pulses for a variety of pacing needs.

It is recognized that aspects of the methods disclosed herein for determining noise corruption of a cardiac electrical signal may be implemented in a medical device that is used for monitoring cardiac electrical signals by sensing circuit 86 and control circuit 80 without having therapy delivery capabilities or in a pacemaker that monitors cardiac electrical signals and delivers cardiac pacing therapies by therapy delivery circuit 84, without high voltage therapy capabilities, such as CV/DF shock capabilities.

Control parameters utilized by control circuit 80 for sensing cardiac events and controlling therapy delivery may be programmed into memory 82 via telemetry circuit 88. Telemetry circuit 88 includes a transceiver and antenna for communicating with external device 40 (shown in FIG. 1A) using RF communication or other communication protocols as described above. Under the control of control circuit 80, telemetry circuit 88 may receive downlink telemetry from and send uplink telemetry to external device 40.

Figure 4:
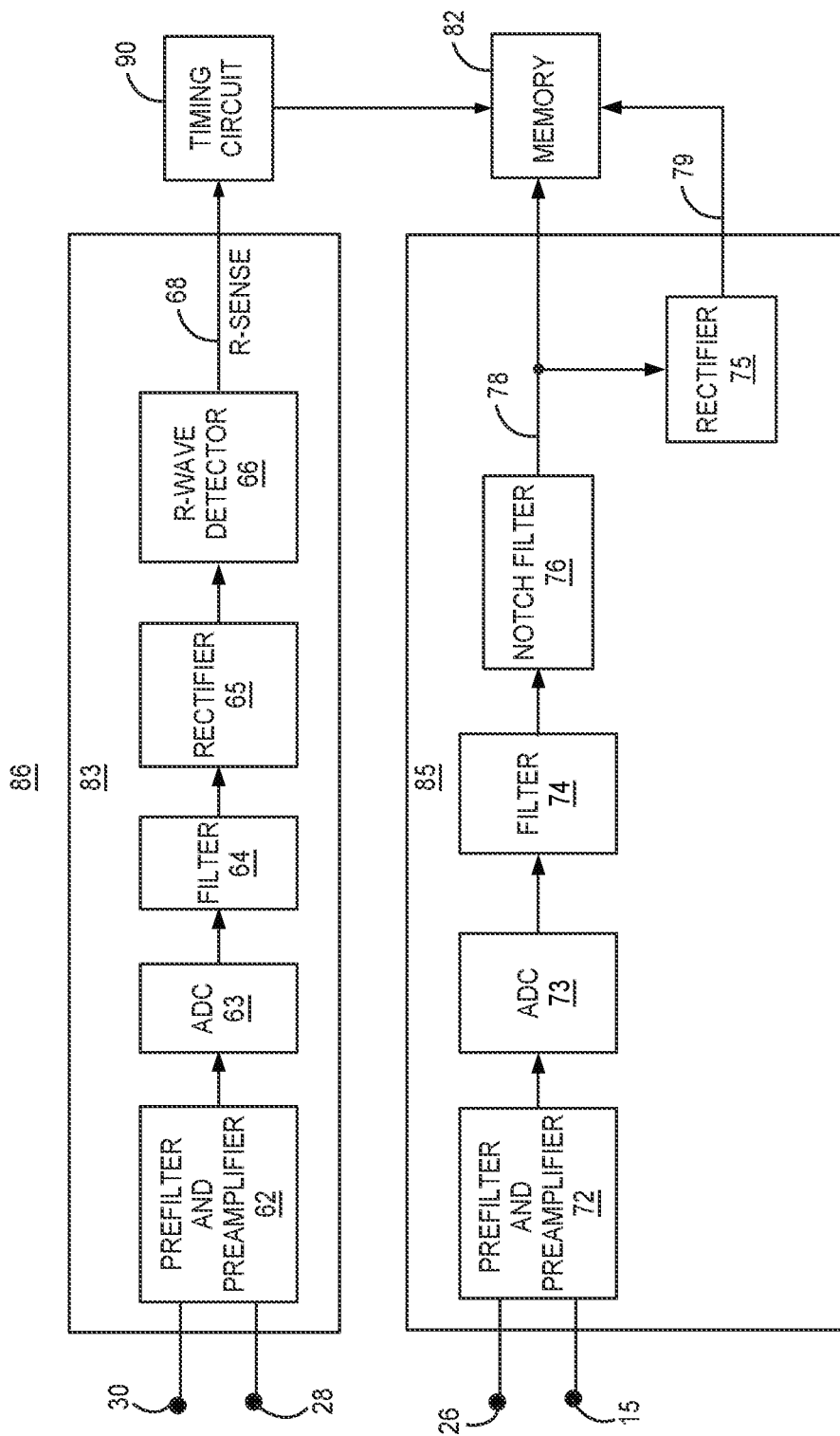
FIG. 4 is a diagram of circuitry that may be included in a sensing circuit of the ICD of FIG. 3.

FIG. 4 is a diagram of circuitry included in sensing circuit 86 having first sensing channel 83 and second sensing channel 85 according to one example. First sensing channel 83 may be selectively coupled via switching circuitry included in sensing circuit 86 to a first sensing electrode vector including at least one electrode carried by extra-cardiovascular lead 16 for sensing a first cardiac electrical signal. In some examples, first sensing channel 83 may be coupled to a sensing electrode vector that is a short bipole, having a relatively shorter inter-electrode distance or spacing than the second electrode vector coupled to second sensing channel 85. First sensing channel 83 may be coupled to a sensing electrode vector that is approximately vertical (when the patient is in an upright position) or approximately aligned with the cardiac axis to increase the likelihood of a relatively high R-wave signal amplitude. In one example, the first sensing electrode vector may include pace/sense electrodes 28 and 30. In other examples, the first sensing electrode vector coupled to sensing channel 83 may include a defibrillation electrode 24 and/or 26, e.g., a sensing electrode vector between pace/sense electrode 28 and defibrillation electrode 24 or between pace/sense electrode 30 and either of defibrillation electrodes 24 or 26. In still other examples, the first sensing electrode vector may be between defibrillation electrodes 24 and 26.

Sensing circuit 86 includes second sensing channel 85 for sensing a second cardiac electrical signal in some examples. For instance, second sensing channel 85 may receive a raw cardiac electrical signal from a second sensing electrode vector, for example from a vector that includes one electrode 24, 26, 28 or 30 carried by lead 16 paired with housing 15. Second sensing channel 85 may be selectively coupled to other sensing electrode vectors, which may form a relatively longer bipole having an inter-electrode distance or spacing that is greater than the sensing electrode vector coupled to first sensing channel 83 in some examples. The second sensing electrode vector may be, but not necessarily, approximately orthogonal to the first channel sensing electrode vector in some cases. For instance, defibrillation electrode 26 and housing 15 may be coupled to second sensing channel 85 to provide the second cardiac electrical signal. As described below, the second cardiac electrical signal received by second sensing channel 85 via a long bipole may be used by control circuit 80 for analysis and detection of noise. The long bipole coupled to second sensing channel 85 may provide a relatively far-field or more global cardiac signal compared to the relatively shorter bipole coupled to the first sensing channel. In other examples, any vector selected from the available electrodes, e.g., electrodes 24, 26, 28, 30 and/or housing 15, may be included in a sensing electrode vector coupled to second sensing channel 85. The sensing electrode vectors coupled to first sensing channel 83 and second sensing channel 85 may be different sensing electrode vectors, which may have no common electrodes or only one common electrode but not both in some examples.

In other examples, however, the sensing electrode vectors coupled to the first sensing channel 83 and the second sensing channel 85 may be the same sensing electrode vector. The two sensing channels 83 and 85 may include different filters, amplifiers, or other signal processing circuitry such that two different signals are sensed by the respective sensing channels 83 and 85 and different analyses may be performed on the two signals. For example, the first sensing channel 83 may sense a first cardiac electrical signal by filtering and processing the received cardiac electrical signal for detecting R-waves in response to an R-wave sensing threshold crossing for determining RRIs. The second sensing channel 85 may sense a second cardiac electrical signal different than the first by filtering and processing the received cardiac electrical signal for passing signal segments to control circuit 80 for analysis for noise detection. The first sensing channel 83 may apply relatively narrower band pass filtering, and the second sensing channel 85 may apply relatively wider band pass filtering and, in some examples, notch filtering to provide two different sensed cardiac electrical signals, received via the same sensing electrode vector.

In the illustrative example shown in FIG. 4, the electrical signals developed across the first sensing electrode vector, e.g., electrodes 28 and 30, are received by first sensing channel 83 and electrical signals developed across the second sensing electrode vector, e.g., electrodes 26 and housing 15, are received by second sensing channel 85. The cardiac electrical signals are provided as differential input signals to the pre-filter and pre-amplifier 62 or 72, respectively, of first sensing channel 83 and second sensing channel 85. Non-physiological high frequency and DC signals may be filtered by a low pass or bandpass filter included in each of pre-filter and pre-amplifiers 62 and 72, and high voltage signals may be removed by protection diodes included in pre-filter and pre-amplifiers 62 and 72. Pre-filter and pre-amplifiers 62 and 72 may amplify the pre-filtered signal by a gain of between 10 and 100, and in one example a gain of 17.5, and may convert the differential signal to a single-ended output signal passed to analog-to-digital converter (ADC) 63 in first sensing channel 83 and to ADC 73 in second sensing channel 85. Pre-filters and amplifiers 62 and 72 may provide anti-alias filtering and noise reduction prior to digitization.

ADC 63 and ADC 73, respectively, convert the first cardiac electrical signal from an analog signal to a first digital bit stream and the second cardiac electrical signal to a second digital bit stream. In one example, ADC 63 and ADC 73 may be sigma-delta converters (SDC), but other types of ADCs may be used. In some examples, the outputs of ADC 63 and ADC 73 may be provided to decimators (not shown), which function as digital low-pass filters that increase the resolution and reduce the sampling rate of the respective first and second cardiac electrical signals.

The digital outputs of ADC 63 and ADC 73 may each be passed to respective filters 64 and 74, which may be digital bandpass filters. The bandpass filters 64 and 74 may have the same or different bandpass frequencies. For example, filter 64 may have a relatively narrow bandpass of approximately 13 Hz to 39 Hz, as an example, for passing cardiac electrical signals such as R-waves typically occurring in this frequency range. Filter 74 of the second sensing channel 85 may have a relatively wider bandpass of approximately 2.5 to 100 Hz as an example. In some examples, second sensing channel 85 may further include a notch filter 76 to filter 60 Hz and/or 50 Hz noise signals and in some cases harmonics of 60 Hz and/or 50 Hz, e.g., 120 Hz and/or 100 Hz.

The narrow bandpass filtered signal in first sensing channel 83 is passed from filter 64 to rectifier 65 to produce a filtered, rectified signal. First sensing channel 83 includes an R-wave detector 66 for sensing cardiac events in response to the first cardiac electrical signal crossing an R-wave sensing threshold. R-wave detector 66 may include an auto-adjusting sense amplifier, comparator and/or other detection circuitry that compares the filtered and rectified cardiac electrical signal to an R-wave sensing threshold in real time and produces an R-wave sensed event signal 68 when the cardiac electrical signal crosses the R-wave sensing threshold outside of a post-sense blanking interval. The R-wave sensing threshold may be a multi-level sensing threshold, e.g., as disclosed in commonly assigned U.S. Pat. No. 10,252,071 (Cao, et al.), incorporated herein by reference in its entirety. Briefly, the multi-level sensing threshold may have a starting sensing threshold value held for a time interval, which may be equal to a tachycardia detection interval or expected R-wave to T-wave interval, then drops to a second sensing threshold value held until a drop time interval expires, which may be 1 to 2 seconds long. The sensing threshold drops to a minimum sensing threshold, which may correspond to a programmed sensitivity sometimes referred to as the "sensing floor," after the drop time interval. In other examples, the R-wave sensing threshold used by R-wave detector 66 may be set to a starting value based on the peak amplitude determined during the most recent post-sense blanking interval and decay linearly or exponentially over time until reaching a minimum sensing threshold. The techniques described herein are not limited to a specific behavior of the sensing threshold or specific R-wave sensing techniques. Instead, one or more decay rates and intervals and/or one or more step-wise adjustments may be utilized to adjust the R-wave sensing threshold.

The wideband filtered digital cardiac electrical signal 78 from second sensing channel 85 may be passed to memory 82 for buffering a segment of the second cardiac electrical signal 78 in response to an R-wave sensed event signal 68 produced by the first sensing channel 83. The wideband filtered signal may be notch filtered prior to being buffered in memory 82. In some examples, output from the wideband filter 74 and output from the notch filter 76 are buffered to provide a pre-notch filtered signal and a post-notch filtered signal for use in the noise determination analyses described below. In some examples, the buffered segment of the second cardiac electrical signal 78 is rectified by rectifier 75 before being stored in memory 82. In some cases, both the filtered, non-rectified signal 78 and the rectified signal 79 are passed to control circuit 80 and/or memory 82 for use in determining features of the second cardiac electrical signal. A feature of the second cardiac electrical signal may be determined from a second cardiac electrical signal segment where each segment extends over a time interval that encompasses the time point of an R-wave sensed event signal produced by the first sensing channel 83.

Control circuit 80 is configured to detect tachyarrhythmia based on cardiac events detected from at least one cardiac electrical signal sensed by sensing circuit 86. For example, control circuit 80 may be configured to detect tachyarrhythmia when a threshold number of sensed cardiac events each occur at a tachyarrhythmia interval. Control circuit 80 may buffer segments of a sensed cardiac electrical signal in memory 82 and retrieve stored signal segments from memory 82 for analysis when a lower threshold number of tachyarrhythmia intervals have been detected, before the tachyarrhythmia detection threshold is reached. In some examples, RRIs for detecting tachyarrhythmia intervals are determined from the first cardiac electrical signal sensed by first sensing channel 83, and cardiac electrical signal segments are buffered from the second cardiac electrical signal received by control circuit 80 from second sensing channel 85 for noise analysis when the lower threshold number of tachyarrhythmia intervals is detected. Analysis of the second cardiac electrical signal segments may be performed for use in detecting non-cardiac noise before the detection threshold number of tachyarrhythmia intervals (NID) is reached, as described below. In other examples, a single cardiac electrical signal sensed by sensing circuit 86 is used for sensing R-waves for determining RRIs and counting tachyarrhythmia intervals and buffering cardiac electrical signal segments for use in determining noise corruption, where each buffered segment may be associated with one sensed R-wave.

The configuration of sensing channels 83 and 85 as shown in FIG. 4 is illustrative in nature and should not be considered limiting of the techniques described herein. The sensing channels 83 and 85 of sensing circuit 86 may include more or fewer components than illustrated and described in FIG. 4 and some components may be shared between sensing channels 83 and 85. For example, one or more of pre-filter and pre-amplifiers 62/72 and/or ADC 63/73 may be shared components between sensing channels 83 and 85 with a single, sensed signal output split to two sensing channels for subsequent processing and analysis. Sensing circuit 86 and control circuit 80 include circuitry configured to perform the functionality attributed to ICD 14 in detecting suspected noise and rejecting or withholding tachyarrhythmia detection in response to determining noise corruption as disclosed herein.

Figure 5:
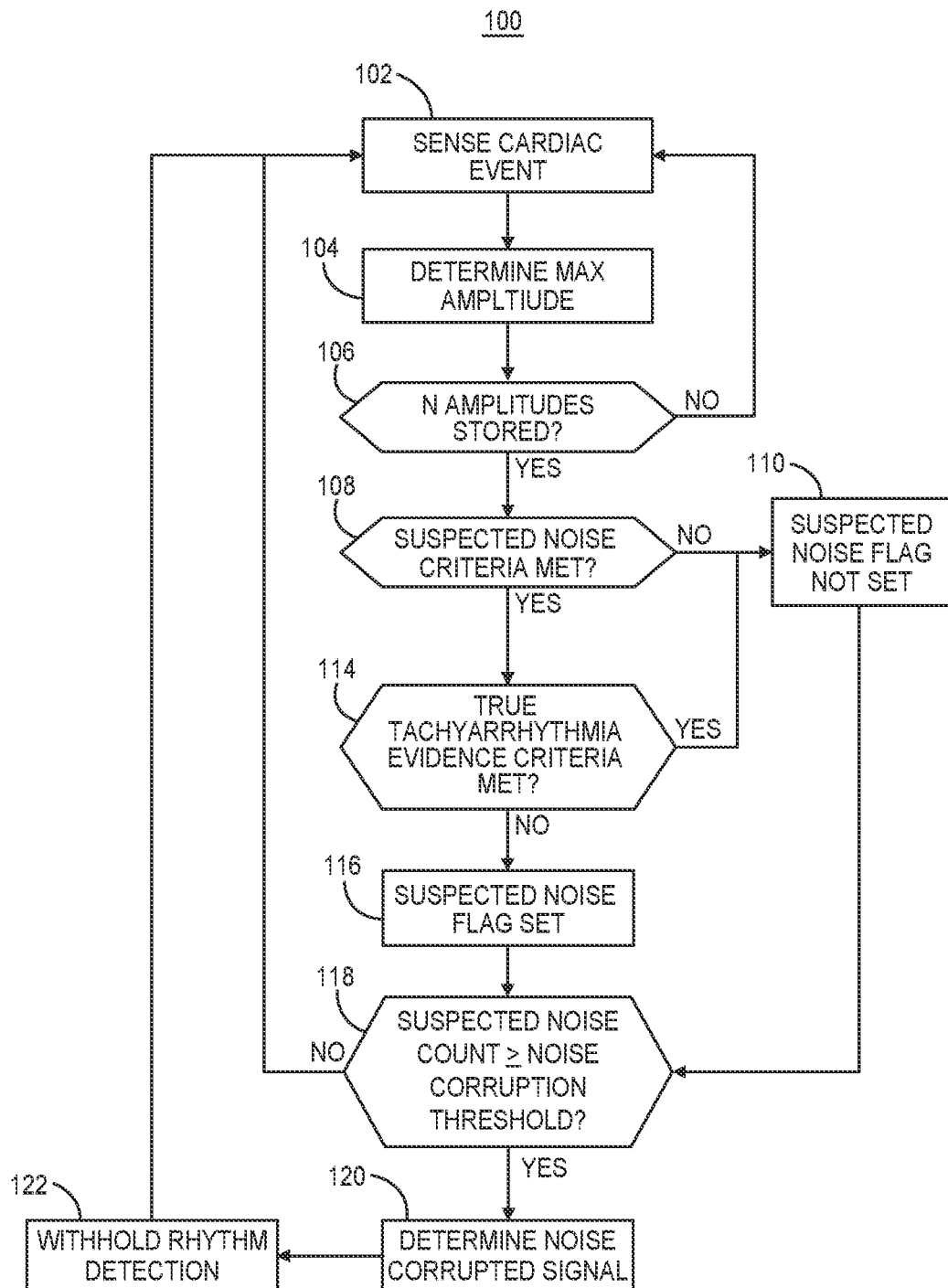
FIG. 5 is a flow chart of a method for determining that a cardiac electrical signal is corrupted by noise according to one example.

FIG. 5 is a flow chart 100 of a method for determining that a cardiac electrical signal is corrupted by noise according to one example. At block 102, sensing circuit 86 senses a cardiac event signal, e.g., an R-wave. Control circuit 80 may determine a maximum amplitude associated with the sensed cardiac event at block 104. In some examples, the maximum amplitude may be determined from the same cardiac electrical signal from which the cardiac event was sensed. In other examples, control circuit 80 may buffer a segment of a different cardiac electrical signal, e.g., the wide band and notch-filtered signal from the second sensing channel 85, in memory 82. The maximum amplitude may be a maximum peak to peak amplitude determined from a segment of the cardiac electrical signal that is buffered over a time interval that includes the time of the cardiac sensed event signal from the first sensing channel 83, e.g., R-wave sensed event signal 68. In other examples, a maximum peak amplitude of a wide band and notch filtered rectified signal may be determined at block 104. The maximum amplitude may be stored in an amplitude buffer in memory 82 that stores a predetermined number of maximum amplitudes, each associated with a sensed cardiac event, in a first in first out basis. Each maximum amplitude may be stored in the amplitude buffer with a timestamp corresponding to the time of the maximum peak or corresponding to the time of the associated sensed event signal. In some instances, a very large signal may saturate the ADC of the sensing channel. In this case, the maximum amplitude may be flagged as invalid in the amplitude buffer. When the signal is clipped, exceeding the ADC input range, the maximum peak to peak amplitude of the input range may be stored as the maximum amplitude but may be labeled as invalid or ignored by control circuit 80 for determining when true tachyarrhythmia evidence criteria are met at block 114 as described below. An over-range amplitude may occur when a large noise signal occurs or when the cardiac electrical signal is erratic.

At block 106, control circuit 80 may determine if a required number of events have been sensed for determining if suspected noise criteria are met at block 108. For example, six to eighteen maximum peak amplitudes may be stored in amplitude buffer in memory 82. In some examples, three to fifteen, e.g., eleven to thirteen, maximum peak amplitudes are stored in the amplitude buffer in memory 82. If a minimum number of maximum amplitudes are not stored in the buffer, the process returns to block 102 until the required number of maximum amplitudes are determined and stored in the amplitude buffer. A minimum number, e.g., at least three maximum amplitudes, may be required in order to determine if suspected noise criteria are met. In some examples, the buffer may be required to be filled. In other examples at least three out of thirteen buffer locations, or another predetermined number of maximum amplitudes, may be required for proceeding to determine if suspected noise criteria are met.

When at least the required number of maximum amplitudes is stored, control circuit 80 may determine if the stored maximum amplitudes meet suspected noise criteria at block 108. Control circuit 80 may apply one or more requirements to the maximum amplitudes stored in the amplitude buffer to determine if suspected noise criteria are met at block 108. In one example, control circuit 80 determines if at least one of the stored peak to peak amplitudes is less than a noise amplitude threshold. In other examples, control circuit 80 may identify two or more of the lowest maximum amplitudes and determine a mean or median of selected number of lowest maximum amplitudes. For instance, control circuit 80 may determine a mean lowest maximum amplitude as the average of the two smallest maximum amplitude values stored in the maximum amplitude buffer. This mean lowest maximum amplitude may be compared to the noise amplitude threshold. The noise amplitude threshold may be set between 0.5 milliVolts (mV) and 2.5 mV, as examples. In one example, the noise amplitude threshold is set to 2.0 mV. When the mean lowest maximum amplitude is less than 2.0 mV (or another selected noise amplitude threshold), the suspected noise criteria may be met at block 108.

In some examples, the noise amplitude threshold may be set based on the peak amplitude of known cardiac events, e.g., based on the peak amplitude of one or more R-waves sensed during a normal, resting heart rate. For instance, a median R-wave amplitude may be determined and the noise amplitude threshold may be set to a fraction of the median R-wave amplitude. The noise amplitude threshold may be set to one-fourth, one fifth, one-sixth or other portion of the sensed R-wave amplitude, as examples.

In other examples, control circuit 80 may determine a ratio of the lowest maximum amplitude to the greatest maximum amplitude from the stored maximum amplitudes. Control circuit 80 may compare the ratio to a threshold ratio. The lowest maximum amplitude, which may be a mean or median lowest maximum amplitude, is determined from one or more of the smallest maximum amplitudes stored in the amplitude buffer. The greatest maximum amplitude, which may be a mean or median greatest maximum amplitude, may be determined from one or more of the highest maximum amplitudes stored in the amplitude buffer. In one example, the ratio of the mean of the two lowest maximum amplitudes to the one greatest maximum amplitude stored in the amplitude buffer is determined and compared to a ratio threshold. The ratio threshold may be set to 2/5, 1/5, 1/6, 1/7, 1/8 or other selected ratio. In one example, the ratio threshold is 1/6. When the ratio of the mean lowest maximum amplitude (e.g., determined as a mean from the smallest two maximum amplitudes) to the single greatest maximum amplitude is less than 1/6, suspected noise criteria are met at block 108.

In some examples, the lowest maximum amplitude (which may be determined as a mean of two or more of the smallest maximum amplitudes stored in the amplitude buffer) may be required to be less than a noise threshold amplitude, e.g., less than 2.0 mV, and the ratio of the lowest maximum amplitude to the greatest maximum amplitude may be required to be less than a ratio threshold, e.g., less than 1/6, for control circuit 80 to determine that suspected noise criteria are met at block 108. The suspected noise criteria generally require that at least one of the stored maximum amplitudes is relatively small, e.g., less than the noise amplitude threshold, as evidence of relatively lower amplitude noise signals which may be present in the wide band and notch filtered signal and that the ratio of the lowest maximum amplitude to the highest maximum amplitude is relatively small, as evidence of at least one relatively large signal which may correspond to a true R-wave or fibrillation wave occurring during noise corruption. As indicated above, a maximum peak to peak amplitude in the amplitude buffer that is equal to the ADC input range (indicating a saturated or clipped signal) may be ignored for the purposes of determining a greatest maximum amplitude used in applying suspected noise criteria in some examples. In other examples, the maximum peak to peak amplitude corresponding to the ADC input range may be used as the highest maximum amplitude when comparing the ratio threshold to the ratio of the lowest maximum amplitude to the highest maximum amplitude.

As another example, applying the suspected noise criteria by control circuit 80 at block 108 may include determining the maximum peak to peak amplitude from the wide band filtered signal segment prior to notch filtering (e.g., output of filter 74 in FIG. 4) and determining the maximum peak to peak amplitude from the wide band and notch filtered signal (e.g., from signal 78 in FIG. 4). Control circuit 80 may determine the ratio of the post-notch filtered maximum peak to peak amplitude to the pre-notch filtered peak to peak amplitude and compare the ratio to a relative noise threshold. The notch filter 76 is expected to attenuate 50-60 Hz noise. Accordingly, the maximum peak to peak amplitude of the notch filtered signal is expected to be significantly lower than the maximum peak to peak amplitude of the wide band filtered signal (output of filter 74) when the R-wave sensed event signal that triggers buffering of the signal segment from the second channel 85 is an oversensed noise signal.

Therefore, when the maximum peak to peak amplitude of the notch filtered signal is associated with a noise signal, the ratio is expected to be low, less than a relative noise threshold ratio. When the maximum peak to peak amplitude is associated with a true cardiac event signal, the true cardiac event signal is expected to be minimally attenuated by notch filtering. In this case, the ratio of the post-notch filtered maximum peak to peak amplitude to the pre-notch filtered maximum peak to peak amplitude is expected to be close to one. Control circuit 80 may set the relative noise threshold between 0.5 and 0.9 or between 0.7 and 0.8 as examples. When the determined ratio associated with at least one sensed cardiac event is less than the relative noise threshold, suspected noise criteria may be met at block 18. When the ratio is greater than the relative noise threshold, the suspected noise criteria may be unmet. In some examples, control circuit 80 may compare the relative noise threshold to the ratio of the post- to pre-notch filtered maximum amplitudes determined for the lowest maximum peak to peak amplitude stored in the amplitude buffer (determined from the post-notch filtered signal). In other examples, control circuit 80 may compare the relative noise threshold to one or more post- to pre-notch filtered maximum amplitude ratios corresponding to maximum peak to peak amplitudes stored in the amplitude buffer associated with sensed cardiac event signals sensed at or less than a tachyarrhythmia interval. In still other examples, control circuit 80 may compare the relative noise threshold to each post- to pre-notch filtered maximum amplitude ratio that corresponds to maximum peak to peak amplitude stored in the amplitude buffer that is less than a noise threshold amplitude.

The suspected noise criteria applied by control circuit 80 at block 108 may be met when at least one maximum peak to peak amplitude is less than the noise threshold amplitude, a ratio of the lowest maximum peak to peak amplitude to the greatest maximum peak to peak amplitude is less than a ratio threshold, and/or a post- to pre-notch filtered maximum amplitude ratio is less than a relative noise threshold or any combination thereof. In various examples, the suspected noise criteria may include one, two, three or more requirements applied to the maximum amplitudes stored in the amplitude buffer. The suspected noise criteria may be met when at least one requirement is met, two out of three requirements are met, or when all specified requirements are met, e.g., two out of two requirements.

When control circuit 80 determines that suspected noise criteria are not met at block 108, control circuit 80 adjusts a counter used to determine how many times suspected noise criteria are met over the most recent N sensed cardiac events. For example, control circuit 80 may move a zero into a first in first out suspected noise buffer in memory 82 configured to store a zero each time suspected noise criteria are not met and a one each time suspected noise criteria are met. The buffer may store the same number of values as the maximum amplitude buffer in some examples but may store a different number of values.

When control circuit 80 determines that the suspected noise criteria are met at block 108, before counting the suspected noise determination by moving a one into the suspected noise buffer, control circuit 80 may verify that true tachyarrhythmia evidence criteria are unmet at block 114. Control circuit 80 may apply true tachyarrhythmia evidence criteria to the maximum amplitude data stored in the amplitude buffer and/or to cardiac signal segments buffered in response to the sensed cardiac events. The true tachyarrhythmia evidence criteria may include one or more interval related requirements applied to time intervals determined between maximum amplitudes stored in the buffer (e.g., based on timestamps or based on the cardiac event intervals, e.g., RRIs, associated with the corresponding sensed event signals, e.g., R-wave sensed event signals). The true tachyarrhythmia evidence criteria may additionally or alternatively include morphology criteria applied to at least one cardiac signal segment buffered in memory and associated with a sensed event signal. The tachyarrhythmia evidence criteria may be applied to determine when evidence of at least one true tachyarrhythmia interval (or true cardiac event interval) is determined and/or evidence of at least one true tachyarrhythmia morphology waveform is determined over the N sensed cardiac events associated with the maximum amplitudes buffered in the amplitude buffer. Techniques for determining true tachyarrhythmia evidence criteria are met at block 114 are described below, e.g., in conjunction with FIGS. 7-10. As indicated above, when a maximum peak to peak amplitude equal to the ADC input range is stored in the amplitude buffer, this over-range amplitude may be ignored by control circuit 80 for the purposes of determining if tachyarrhythmia evidence criteria are met since an over-range signal is unlikely to be a true cardiac event signal.

When control circuit 80 determines that true tachyarrhythmia evidence criteria is met at block 114, control circuit 80 may move a zero into the suspected noise buffer at block 110. Even though the suspected noise criteria were met at block 108, evidence of a true tachyarrhythmia event prevents control circuit 80 from counting the suspected noise determination toward a determination of noise corruption in the cardiac electrical signal used to withhold a tachyarrhythmia detection. In this way, control circuit 80 inhibits determining noise corruption that would withhold a tachyarrhythmia detection when other cardiac signal evidence suggests that the true underlying rhythm may be tachyarrhythmia.

When control circuit 80 determines that the true tachyarrhythmia evidence criteria are not met at block 114, control circuit 80 may count the suspected noise determination at block 116, e.g., by setting a suspected noise flag. For instance, control circuit 80 may move a one into a first in first out suspected noise buffer to facilitate counting suspected noise determinations. The size of the suspected noise buffer configured to store a suspected noise determination as a 1 or a 0 may be between 6 and 18 and is 12 in one example. At block 118, control circuit 80 may compare the suspected noise determination count to a noise corruption threshold. For example, control circuit 80 may count the number of ones stored in the suspected noise buffer. When the suspected noise count is greater than or equal to a noise corruption threshold, control circuit 80 may determine noise corruption of the cardiac electrical signal 120. For instance, control circuit 80 may determine noise corruption of the cardiac electrical signal at block 120 in response to at least three suspected noise determinations over of the most recent twelve sensed cardiac events. It is noted that a suspected noise signal may not correspond to the currently sensed cardiac event. Rather, one or more of the maximum amplitudes stored in the amplitude buffer may correspond to a noise signal, which may be any of the most recent sensed events corresponding to the stored maximum amplitudes, when suspected noise criteria are met.

In response to determining noise corruption control circuit 80 may withhold making a rhythm detection or heart rate determination at block 122. In the examples described herein, control circuit 80 may withhold detecting a tachyarrhythmia based on other tachyarrhythmia detection criteria being met when a noise corruption determination is made.

Figure 6:
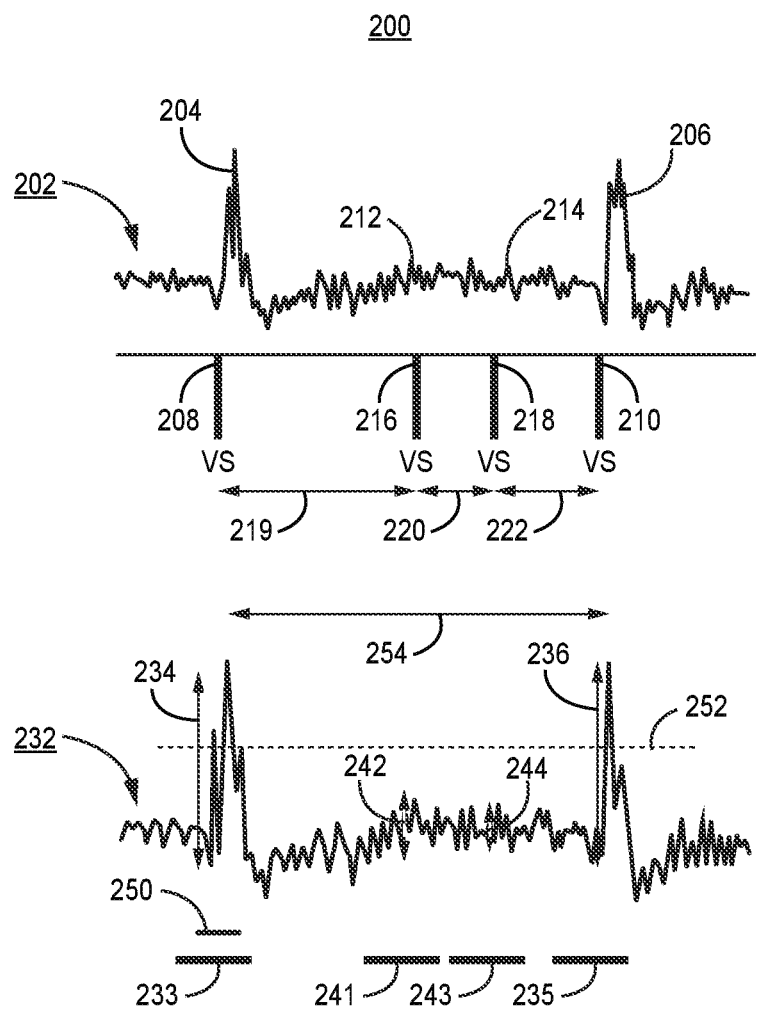
FIG. 6 is diagram of a first cardiac electrical signal and a second cardiac electrical signal that may be used for sensing cardiac events and determining noise corruption according to one example.

FIG. 6 is diagram 200 of a first cardiac electrical signal 202 and a second cardiac electrical signal 232 that may be used for sensing cardiac events and determining noise corruption according to one example. In the first cardiac electrical signal 202, two true R-waves 204 and 206 are sensed by the first sensing channel 83 resulting in respective R-wave sensed events signals 208 and 210 (labeled "VS"). However, due to non-cardiac noise present in the first cardiac electrical signal 202, two noise signals 212 and 214 are each sensed by R-wave detector 66 resulting in false R-wave sensed events signals 216 and 218. Each of the R-wave sensed event signals 208, 210, 216 and 218, denoted by "VS" to indicate a ventricular sensed event, trigger buffering of a segment of the second cardiac electrical signal 232 over a respective time interval 233, 235, 241, and 243.

Each time interval 233, 235, 241, and 243 may extend before and after the time of the respective R-wave sensed event signal 208, 210, 216, and 218 such that the associated buffered second cardiac electrical signal segment includes sample points before and after the time of the associated R-wave sensed event signal. Each time interval 233, 235, 241 and 243 may be about 360 ms in duration so that the respective second cardiac electrical signal segment buffered over the time interval includes 92 sample points when the sampling rate is 256 Hz with 24 of the sample points occurring after the R-wave sensed event signal that triggered the storage of the signal segment and 68 sample points extending from the R-wave sensed event signal earlier in time from the R-wave sensed event signal. Each cardiac electrical signal segment may be longer or shorter than 360 ms, but each cardiac electrical signal segment buffered over the respective time interval 233, 235, 241 or 243 encompasses the time of one, single R-wave sensed event signal. If an R-wave sensed event signal occurs before the end of the buffering time interval for an immediately preceding R-wave sensed event signal, control circuit 80 may skip buffering a time segment for that R-wave sensed event signal.

The buffered signal segments may be notch filtered prior to determining maximum peak to peak amplitude data from the signal segments in some examples. Control circuit 80 determines a maximum peak to peak amplitude 234 of the buffered cardiac electrical signal segment from the sample points within time interval 233. Maximum peak to peak amplitude 242 is determined from the buffered cardiac electrical signal segment within time interval 241, and maximum peak to peak amplitudes 244 and 236 are determined from the cardiac electrical signal segments buffered within respective time intervals 243 and 235. Control circuit 80 may determine each maximum peak to peak amplitude 234, 236, 242 and 244 by determining the difference between a maximum sample point amplitude and a minimum sample point amplitude determined from the second cardiac electrical signal sample points within each respective time interval 233, 235, 241 or 243. In some examples, the maximum peak to peak amplitudes 234, 236, 241 and 244 may be determined from sample points occurring within a portion of the respective time interval 233, 235, 241 or 243. For example, each time interval may be at least 300 ms long, e.g., 360 ms or longer. The maximum peak to peak amplitude 234 may be determined as the difference between the maximum sample point and the minimum sample point occurring within a shorter time interval 250 within time interval 233. Time interval 250 may be 200 ms or less in some examples. For instance, when time interval 233 is 360 ms, time interval 250 may be 188 ms and includes the time point of R-wave sensed event signal 208. For a 256 Hz sampling rate, the 188 ms time interval may include 48 sample points centered on the time point of the R-wave sensed event signal 208. Likewise, maximum peak to peak amplitudes 236, 242 and 244 may be determined from sample points occurring over a shortened portion of respective time intervals 235, 241 and 243.

These maximum peak to peak amplitudes 234, 242, 244 and 236 may be stored in a first-in-first-out amplitude buffer in memory 82 so that the maximum peak to peak amplitude of each one of multiple second cardiac electrical signal segments, associated with each R-wave sensed event signal 208, 210, 216 and 218, is buffered in a rolling, first-in-first-out amplitude buffer. The amplitude buffer may store a predetermined number of maximum amplitudes, e.g., 3 to 20 maximum amplitudes corresponding to the most recent 3 to 20 cardiac electrical signal segments and associated R-wave sensed event signals. In one example, at least 10 to 13 maximum amplitudes are stored.

Each of the maximum peak to peak amplitudes 234, 236, 242 and 244 may be stored with a timestamp or an associated cardiac event interval, e.g., RRI, determined by timing circuit 90 for the associated R-wave sensed event signal 208, 210, 216 or 218 (from the most recent preceding R-wave sensed event signal). Maximum peak to peak amplitude 242 may be stored with the RRI 219, which is the time interval between the R-wave sensed event signal 216 associated with maximum peak to peak amplitude 242 and the immediately preceding R-wave sensed event signal 208. Maximum peak to peak amplitude 244 may be stored with RRI 220, and maximum peak to peak amplitude 236 may be stored with RRI 222, for example.

Control circuit 80 may apply suspected noise criteria to the buffered maximum peak to peak amplitudes 234, 236, 242 and 244, e.g., as described above in conjunction with FIG. 5 at block 108. When the suspected noise criteria are met, control circuit 80 may analyze the morphology of at least one second cardiac electrical signal segment stored over a respective time interval, which may be all or a portion of the respective time interval 233, 235, 241 or 243, to verify that a tachyarrhythmia morphology is not present before determining suspected noise and setting a suspected noise flag. For example, control circuit 80 may identify the greatest maximum peak to peak amplitude that is stored in the maximum amplitude buffer. For instance, peak to peak amplitude 234 in the example shown in FIG. 6 may be the greatest maximum amplitude stored. Control circuit 80 may determine one or more gross morphology metrics as described below in conjunction with FIGS. 9 and 10 based on at least a signal segment corresponding to the greatest maximum peak to peak amplitude 234 in the amplitude buffer. Control circuit 80 may be configured to determine if the morphology of the cardiac signal segment associated with the greatest maximum amplitude meets true tachyarrhythmia evidence criteria (e.g., at block 114 of FIG. 5). If so, control circuit 80 may not determine suspected noise and, in response, move a zero into the suspected noise buffer. If control circuit 80 determines that the gross morphology metric does not meet true tachyarrhythmia evidence criteria, control circuit 80 may determine suspected noise and move a one into the suspected noise buffer. As described below, the gross morphology metric may be determined using all sample points spanning the time interval 233 over which the cardiac electrical signal segment is buffered. In some examples, a gross morphology amplitude metric and a gross morphology signal width metric may be determined. When control circuit 80 determines that at least one gross morphology metric does not meet the true tachyarrhythmia evidence criteria, control circuit 80 may determine suspected noise based on the analysis of the maximum peak to peak amplitudes stored in the amplitude buffer.

In some examples, control circuit 80 may analyze the timestamps or associated RRIs 219, 220 222 that may be stored with each maximum peak to peak amplitude. As described below in conjunction with FIG. 7, control circuit 80 may analyze intervals between the sensed events associated with the maximum peak to peak amplitudes for determining if interval-based criteria of true tachyarrhythmia evidence are met at block 114 of FIG. 5. For example, control circuit 80 may identify buffered maximum amplitudes 234 and 236 that are greater than a threshold amplitude 252 as suspected true cardiac events. As described below in conjunction with FIG. 7, the threshold amplitude 252 may be set to percentage or fraction of the greatest maximum amplitude 234. In one example, control circuit 80 sets the threshold amplitude 252 to five-eighths of the greatest maximum amplitude 234. Using the timestamps or associated RRIs stored with each of the buffered maximum amplitudes, control circuit 80 may determine a time interval 254 between two consecutive maximum peak to peak amplitudes that are greater than the threshold amplitude 252. This time interval 254 may be determined as a suspected true cardiac event interval. When this time interval falls within a tachyarrhythmia interval range, control circuit 80 may determine evidence of a true tachyarrhythmia.

Figure 7:
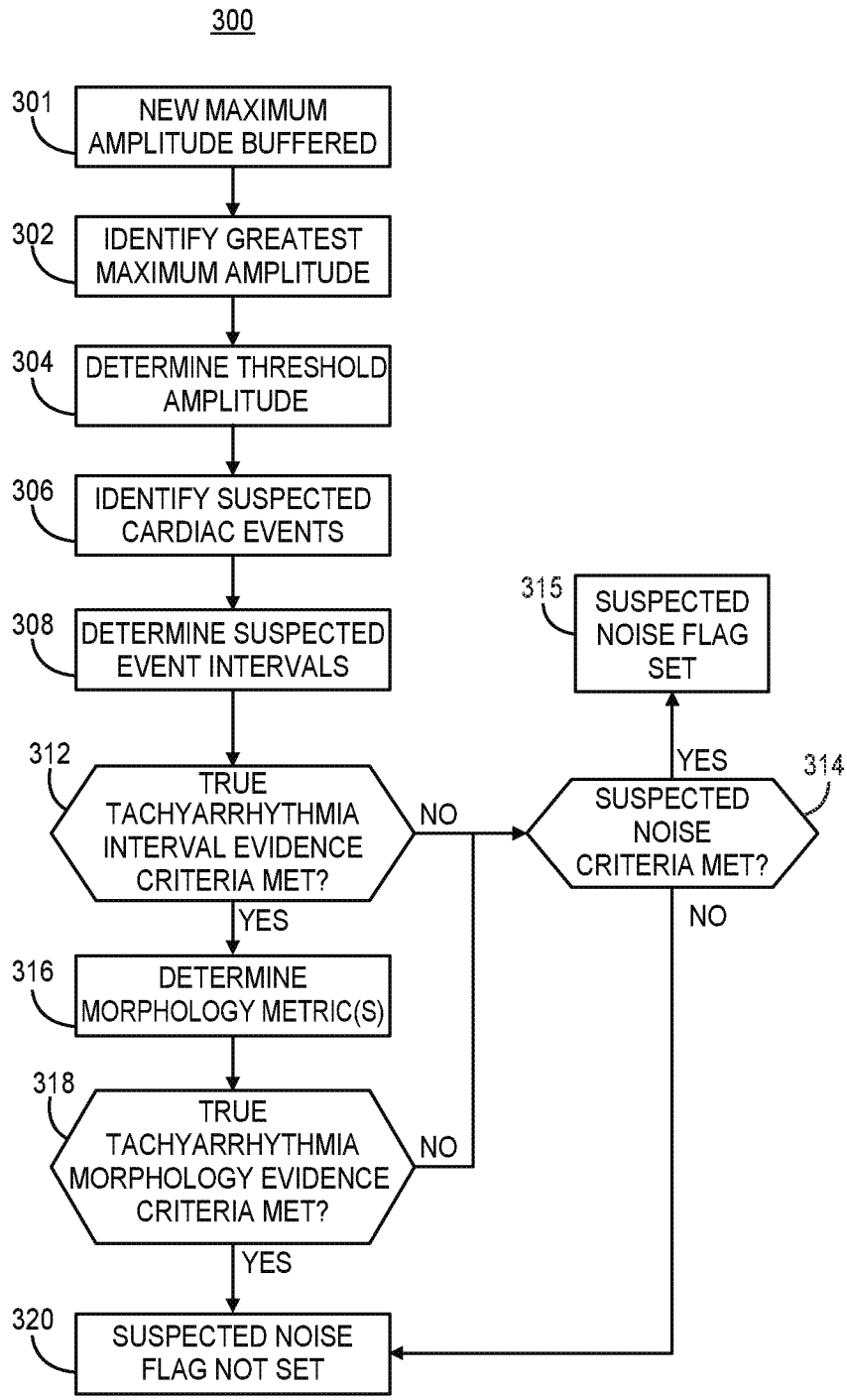
FIG. 7 is a flow chart of a method for determining when tachyarrhythmia evidence criteria are not met for enabling a determination of suspected noise corruption according to one example.

FIG. 7 is a flow chart 300 of a method for determining when tachyarrhythmia evidence criteria are not met so that a determination of suspected noise can be made based on buffered maximum amplitudes according to one example. At block 301, control circuit 80 moves a new maximum peak to peak amplitude into the amplitude buffer. Control circuit 80 may determine the new maximum peak to peak amplitude from a portion of a cardiac electrical signal segment buffered in response to a cardiac sensed event signal as described above in conjunction with FIG. 5.

At block 302, control circuit 80 identifies a greatest maximum amplitude from among the buffered maximum amplitudes in the amplitude buffer. At block 304, control circuit 80 determines a threshold amplitude, which may be based on the buffered maximum amplitudes. The threshold amplitude, e.g., threshold amplitude 252 in FIG. 6, may be based on the greatest maximum amplitude identified at block 302. For example, control circuit 80 may identify the greatest maximum amplitude and set the threshold amplitude as a percentage or fraction of the greatest maximum amplitude. For instance, the threshold amplitude may be set to 50% to 80% of the greatest maximum amplitude. In one example, control circuit 80 sets the threshold amplitude to five-eighths of the greatest maximum amplitude. In other examples, control circuit 80 may identify two or more of the highest maximum amplitudes in the amplitude buffer and determine the threshold amplitude at block 304 based on two or more of the highest maximum amplitudes. For example, the threshold amplitude may be set to a percentage or fraction of a mean, median, or nth highest maximum amplitude determined from two or more of the highest maximum amplitudes. The threshold amplitude may alternatively be a predetermined, programmed value.

The threshold amplitude is set to discriminate between signals that are suspected true cardiac event signals and suspected noise signals based on amplitude. At block 306, control circuit 80 compares each buffered maximum amplitude value to the threshold amplitude to identify suspected true cardiac events. Each buffered maximum amplitude value that is greater than the threshold amplitude is identified as a suspected true cardiac event, e.g., a true R-wave. Based on the timestamp or sensed event interval stored with each of the identified suspected true cardiac events, control circuit 80 may determine event intervals associated with the suspected true cardiac events at block 308. For example, control circuit 80 may determine the time interval between two maximum amplitudes identified as consecutive suspected true cardiac events. The time interval may be determined by control circuit 80 as the difference between the timestamps of two maximum amplitudes that are both greater than the threshold amplitude and are therefore consecutive suspected true cardiac events. The time interval may alternatively be determined based on cardiac event intervals, e.g., RRIs, determined by timing circuit 90 between consecutive sensed event signals. For instance, control circuit 80 may determine the suspected event interval by summing all intervening RRIs between two consecutive sensed event signals associated with maximum amplitudes greater than the threshold amplitude. Control circuit 80 may determine the suspected cardiac event interval by summing two or more consecutive RRIs that occur between two maximum amplitudes that are identified as suspected true cardiac events.

With reference to FIG. 6, as an example, control circuit 80 may determine that the maximum peak to peak amplitudes 234 and 236 are greater than the threshold amplitude and maximum peak to peak amplitudes 242 and 244 are less than the threshold amplitude. As a result, control circuit 80 may determine a suspected true cardiac event interval as the time interval from VS signal 208 to VS signal 210. Control circuit 80 may sum the RRIs 219, 220 and 222 occurring between the VS event signals 208 and 210 that are associated with two consecutive maximum peak to peak amplitudes that are greater than the threshold amplitude 252. As noted above, in other examples control circuit 80 may determine the difference between a timestamp stored for maximum peak to peak amplitude 234 and maximum peak to peak amplitude 236 as the suspected true cardiac event interval.

Returning to FIG. 7, in some instances, a single suspected true cardiac event interval may be determined at block 308. In other instances, two or more suspected true cardiac event intervals may be determined, or no suspected true cardiac event intervals may be determined by control circuit 80 based on the buffered maximum amplitudes. The number of suspected true cardiac event intervals determined at block 308 depends on the number of suspected cardiac events identified from the buffered maximum amplitudes at block 306. When the threshold amplitude is set based on the greatest maximum amplitude in the amplitude buffer, at least the one greatest maximum amplitude will be identified as being associated with a suspected true cardiac event. A single suspected true cardiac event identified at block 306 may yield no determinable value of a suspected true cardiac event interval from the buffered data since two maximum amplitudes greater than the threshold amplitude are not available for determining a value of the suspected true cardiac event interval.

If only one suspected true cardiac event is identified at block 306, the event may be a noise spike or a true R-wave or fibrillation wave. The remaining buffered maximum amplitudes may be associated with noise signals or low amplitude fibrillation waves. A true cardiac event interval associated with the one suspected true cardiac event may extend earlier than the timestamp of the oldest buffered maximum amplitude. The suspected true cardiac event interval value, however, is indeterminable. It may be assumed to be greater than the time interval to the oldest buffered maximum amplitude or the single event having the greatest maximum amplitude may be a noise signal. In this case, control circuit 80 may determine that true tachyarrhythmia interval criteria are met at block 312 in order to advance to block 316 to perform morphology analysis. Morphology analysis may be performed for detecting true tachyarrhythmia evidence when a suspected true cardiac event interval is indeterminable due to a single suspected true cardiac event being identified.

Control circuit 80 may determine one single suspected true cardiac event interval at block 308 when only two suspected true cardiac events are identified at block 306. When three or more suspected true cardiac events are identified at block 304, control circuit 80 may determine two or more suspected true cardiac event intervals (n−1 intervals when n suspected true cardiac events are identified). When at least one suspected true cardiac event interval is determined at block 308, control circuit 80 may compare the suspected true cardiac event interval(s) to true tachyarrhythmia interval evidence criteria at block 312. In one example, if at least one suspected true cardiac event interval falls within a true tachyarrhythmia evidence interval range, the true tachyarrhythmia interval evidence criteria may be determined to be met by control circuit 80.

The true tachyarrhythmia evidence interval range may be based on a programmed tachyarrhythmia detection interval or set to a predetermined range in various examples. For instance, when VT detection is enabled, the true tachyarrhythmia evidence interval range may have an upper limit set based on the VT detection interval, e.g., the VT detection interval plus an offset. If VT detection is disabled, the true tachyarrhythmia evidence interval range may have an upper limit set based on the VF detection interval, e.g., the VF detection interval pulse an offset. As described above, a programmed VF detection interval may be 320 ms as an example. A programmed VT detection interval may be 400 ms as an example. The offset may range from 0 ms to 60 ms and is 40 ms in one example, with no limitation intended. Accordingly, the upper limit of true tachyarrhythmia evidence interval criteria applied at block 312 may be 360 ms to 440 ms as examples. The lower limit may be set based on a programmed detection interval or set to a predetermined value. The lower limit may be between 150 ms and 220 ms and is 190 ms in one example. Event intervals shorter than the lower limit may be noise intervals.

When at least one suspected cardiac event interval is determined at block 308 and none fall within the true tachyarrhythmia evidence interval range at block 312, control circuit 80 may advance to block 314 to determine whether the buffered maximum amplitudes meet suspected noise criteria. The determination of whether suspected noise criteria are met may correspond to the techniques described above in conjunction with FIG. 5. For example, the lowest maximum amplitude may be required to be less than a noise threshold amplitude, e.g., less than 2.0 mV, and the ratio of the lowest maximum amplitude to the greatest maximum amplitude may be required to be less than a ratio threshold, e.g., less than 1/6. The lowest maximum amplitude may be a mean or median of two or more of the smallest maximum amplitudes or the single lowest maximum amplitude in the amplitude buffer. When the suspected noise criteria are met at block 314, a suspected noise flag is set at block 315, e.g., by moving a one into a suspected noise buffer to enable counting of the number of suspected noise determinations out of the most recent n sensed events. Suspected noise is detected by control circuit 80 in the absence of true tachyarrhythmia interval evidence determined from the buffered maximum amplitudes. The true tachyarrhythmia interval evidence is based at least on the greatest maximum amplitude used to determine the amplitude threshold and used to determine whether at least one suspected event interval meets the true tachyarrhythmia interval evidence. When the suspected noise criteria are unmet at block 314, the suspected noise flag is not set at block 320, e.g., by moving a zero into the suspected noise buffer. In the example of flow chart 300, therefore, suspected noise criteria may be applied to the buffered maximum amplitudes when interval-based tachyarrhythmia evidence criteria are unmet.

When control circuit 80 determines that at least one suspected true cardiac event interval meets the tachyarrhythmia interval evidence criteria at block 312, control circuit 80 may advance to block 316 to determine if morphology based tachyarrhythmia evidence criteria are met before applying suspected noise criteria at block 314. At block 316, control circuit 80 determines at least one morphology metric from at least one cardiac signal segment buffered in response to a cardiac sensed event signal. In some examples, control circuit 80 identifies the greatest maximum amplitude stored in the amplitude buffer. Control circuit 80 may determine the morphology metric at block 316 from the buffered cardiac electrical signal segment from which the greatest maximum amplitude was determined.

Example techniques for determining the morphology metrics at block 316 are described below in conjunction with FIGS. 8-10. The morphology metrics may include a gross morphology amplitude metric determined from the cardiac electrical signal segment associated with the greatest maximum amplitude, e.g., using the techniques described in conjunction with FIG. 9. The gross morphology amplitude metric is compared to true tachyarrhythmia morphology evidence criteria at block 318. When the gross morphology amplitude metric is relatively high, the associated cardiac electrical signal is a relatively large signal which may be a true fibrillation waveform or R-wave as opposed to a narrow noise signal spike or relatively smaller baseline noise signal. Therefore a gross morphology amplitude metric that is greater than a threshold may be determined to be evidence of a true cardiac event as opposed to oversensed noise and is determined to be true tachyarrhythmia evidence by control circuit 80.

The morphology metrics determined at block 316 may include a gross morphology signal width metric. The gross morphology signal width metric may be determined using the techniques described in conjunction with FIG. 10. When the signal width metric may also be determined by control circuit 80 from the cardiac signal segment associated with the greatest maximum amplitude stored in the amplitude buffer. When the gross morphology signal width metric is relatively high, the associated cardiac electrical signal is a relatively wide signal that has a higher likelihood of being a true fibrillation wave than a noise signal. As such, control circuit 80 may determine evidence of a true tachyarrhythmia at block 318 in response to a gross morphology signal width metric being greater than a threshold value.

Example criteria applied at block 318, such as a threshold value applied to a gross morphology amplitude metric and a threshold value applied to a gross morphology signal width metric are described below in conjunction with FIGS. 9 and 10. In some examples, the true tachyarrhythmia morphology evidence criteria are applied only to morphology metrics determined from the buffered cardiac signal segment associated with the greatest maximum amplitude in the amplitude buffer. It is to be understood, however, that the true tachyarrhythmia morphology evidence criteria may be applied to morphology metrics determined from more than one buffered cardiac signal segment. For example, the true tachyarrhythmia morphology evidence criteria may be applied to all cardiac electrical signal segments associated with the buffered maximum amplitudes that are greater than the amplitude threshold. When control circuit 80 determines that true tachyarrhythmia morphology evidence criteria are met at block 318, a suspected noise flag is not set at block 320. The determination of no suspected noise at block 320 may be made by control circuit 80 without determining whether suspected noise criteria are met by the buffered maximum amplitudes. The maximum amplitudes may satisfy suspected noise criteria; however, a suspected noise determination is not made when true tachyarrhythmia morphology evidence criteria are met. Control circuit 80 does count a suspected noise determination for withholding a tachyarrhythmia detection or therapy when the interval-based and morphology-based tachyarrhythmia evidence criteria are both satisfied, indicating that the true underlying rhythm is likely to be a tachyarrhythmia.

In some examples, when both of the gross morphology amplitude metric and the gross morphology signal width metric are greater than a respective threshold value, true tachyarrhythmia morphology evidence criteria are met at block 318. Control circuit 80 may move a zero into the suspected noise buffer at block 310, with or without determining if the buffered maximum amplitudes meet the suspected noise criteria. When at least one gross morphology metric is not greater than a threshold value, true tachyarrhythmia morphology evidence criteria is not met at block 318. Control circuit 80 may advance to block 314 to determine if the buffered maximum amplitudes meet the suspected noise criteria. If so, a one may be moved into the suspected noise buffer at block 316 (or a suspected noise count may be increased). If not, a zero may be moved into the suspected noise buffer at block 320 (or a suspected noise count may be left at the same value or decreased).

Figure 8:
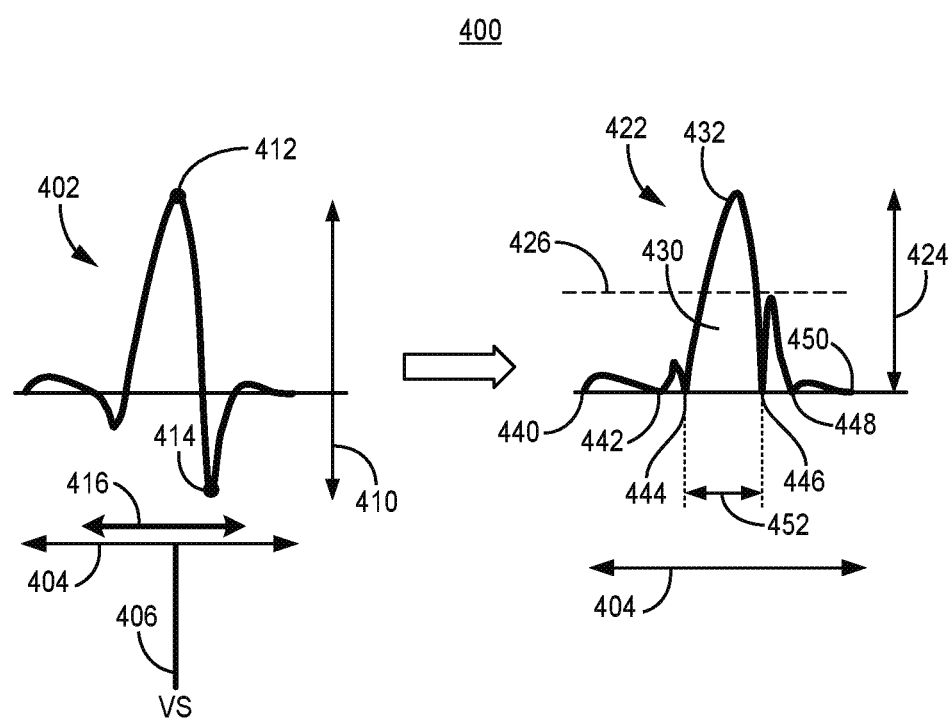
FIG. 8 is a diagram of a cardiac electrical signal segment stored in response to an R-wave sensed event signal.

FIG. 8 is a diagram 400 of a cardiac electrical signal segment 402 stored over time interval 404 in response to an R-wave sensed event signal 406 and a rectified cardiac electrical signal segment 422. In some examples, cardiac electrical signal segment 402 is the wideband, notch filtered signal 78 from second sensing channel 85 of FIG. 4, buffered into memory 82 over time interval 404 in response to an R-wave sensed event signal 406 produced by the first sensing channel 83. The cardiac electrical signal 402 (e.g., from second sensing channel 85) may be buffered in memory 82 at a desired sampling rate, e.g., 128 Hz or 256

Hz, until an R-wave sensed event signal 406 is received at which point the desired number of sample points preceding the R-wave sensed event signal 406, e.g., 68 sample points when the sampling rate is 256 Hz, and the desired number of sample points following the R-wave sensed event signal 406, e.g., 24 sample points occurring after the R-wave sensed event signal 406, are stored in memory 82, in a designated buffer, as the second cardiac electrical signal segment 402 associated with R-wave sensed event signal 406. In other examples, a higher or lower sampling rate may be used, e.g., a sampling rate of 512 Hz or 128 Hz. A correspondingly higher or lower number of sample points may be buffered to analyze the cardiac signal segment 402 over the same or similar time interval 404, extending before and after the time point of the R-wave sensed event signal 406. Time interval 404 over which cardiac electrical signal segment 402 is stored for analysis may be between 100 ms and 500 ms in length in various examples and is 360 ms in one example.

Control circuit 80 determines the maximum peak to peak amplitude 410 as described above for storing in the amplitude buffer, e.g., with a timestamp of the R-wave sensed event signal 406. Maximum peak to peak amplitude 410 may be determined by control circuit 80 as the difference between the maximum amplitude sample point 412 and the minimum amplitude sample point 414. The maximum amplitude sample point 412 and the minimum amplitude sample point 414 may be identified from the sample points spanning a portion of the cardiac electrical signal segment 402, e.g., over a time interval 416 that is shorter than the time interval 404. In one example, time interval 404 is 360 ms and time interval 416 is 188 ms. The maximum peak to peak amplitude 410 is determined from the cardiac electrical signal segment over time interval 416 and gross morphology metrics are determined from the rectified cardiac electrical signal segment 422 spanning the longer time interval 404.

Control circuit 80 may identify maximum peak to peak amplitude 410 as the greatest maximum amplitude stored in the maximum amplitude buffer. The cardiac electrical signal segment associated with the greatest maximum amplitude may be used by control circuit 80 for determining morphology metrics at block 316 of FIG. 7 or block 114 of FIG. 5. Control circuit 80 may determine the gross morphology amplitude metric and the gross morphology signal width metric from the rectified cardiac electrical signal segment 422 in response to the interval based true tachyarrhythmia evidence criteria being met (e.g., as described in conjunction with FIG. 7) or in response to suspected noise criteria being met (e.g., as described in conjunction with FIG. 5).

Figure 9:
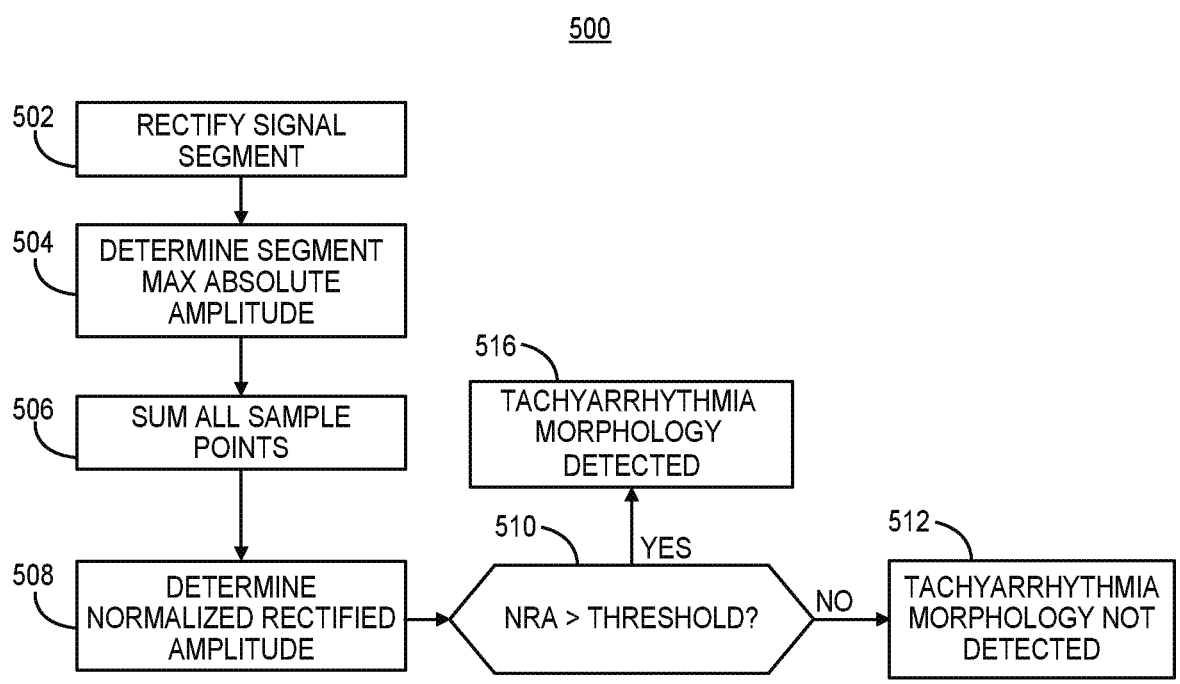
FIG. 9 is a flow chart of a method for determining a gross morphology amplitude metric of a cardiac electrical signal segment for detecting a tachyarrhythmia morphology according to one example.

FIG. 9 is a flow chart 500 of a method for determining a gross morphology amplitude metric of a cardiac electrical signal segment for detecting a tachyarrhythmia morphology according to one example. With reference to FIGS. 8 and 9, at block 502, the cardiac electrical signal segment 402 stored on a triggered basis in response to an R-wave sensed event signal 406 may be rectified to produce the rectified signal 422. In some examples, a 360 ms segment of the notch-filtered second cardiac electrical signal may be rectified by rectifier 75 included in second sensing channel 85 (FIG. 4). At block 502, the buffered, rectified signal segment may be retrieved by control circuit 80 from memory 82. In other examples, a wideband and notch-filtered signal segment 402 may be buffered in memory 82, and control circuit 80 may perform the rectification of the stored signal segment at block 502.

At block 504, control circuit 80 determines the maximum absolute amplitude 424 (shown in FIG. 8) of the rectified, notch-filtered signal segment 422. The maximum absolute amplitude 424 may be determined from among all sample points spanning time interval 404 over which the rectified signal segment 422 is buffered. As described above, a 360 ms segment of the second cardiac electrical signal may include 92 sample points when the sampling rate is 256 Hz, with 24 of the sample points occurring after the R-wave sensed event signal 406 that triggered the storage of the signal segment 402 and 68 sample points extending from the R-wave sensed event signal 406 earlier in time from the R-wave sensed event signal 406.

At block 506, control circuit 80 sums the amplitudes of all sample points of the rectified signal segment 422, which represents the area 430 of the rectified signal segment 422. At block 508, control circuit 80 may determine the gross morphology amplitude metric of the signal segment 422 as a normalized rectified amplitude (NRA) based on the maximum absolute amplitude 424 determined at block 504 and the summed sample point amplitudes (area 430) determined at block 506. In one example, the NRA is determined as a predetermined multiple or weighting of the summation of all sample point amplitudes of the wideband, notch-filtered and rectified signal segment 422 normalized by the maximum absolute amplitude 424. For instance, the NRA may be determined as four times the summed amplitudes (area 430) divided by the maximum absolute amplitude 424, which may be truncated to an integer value. This NRA may be determined as the gross morphology amplitude metric at block 316 of FIG. 7 (or block 114 of FIG. 5) for detecting evidence of a true tachyarrhythmia R-wave or fibrillation wave based on the sample points spanning the signal segment 422 that extends before and after the R-wave sensed event signal 406. As represented in the diagram 400 of FIG. 8, the gross morphology amplitude metric determined from the maximum absolute amplitude 424 and area 430 represents an amplitude metric of the rectified cardiac signal waveform 422 that may correspond to a tachyarrhythmia waveform morphology.

For example, the gross morphology amplitude metric determined as the weighted area 430 divided by the maximum amplitude 424 may be inversely correlated to the probability of the signal segment sample points being at a baseline amplitude during the time interval 404. The higher the gross morphology amplitude metric is, the lower the probability that the signal is at a baseline amplitude at any given time point during the time interval 404. A relatively low probability that the signal 422 is at baseline during the time interval 404 may be correlated to a tachyarrhythmia morphology, e.g., a ventricular fibrillation morphology, which may resemble a sinusoidal signal. When the gross morphology amplitude metric exceeds a threshold value the more likely the cardiac electrical signal segment has a tachyarrhythmia morphology. When the gross morphology amplitude metric is less than the threshold value, the higher the probability that the signal is at a baseline amplitude at a given time point during the time interval 404 of the signal segment 422 or is a relatively small signal. A relatively higher probability of a signal sample point being at or near baseline during the time segment 404 may be correlated to a relatively narrow R-wave signal occurring during the signal segment, or no true R-wave being present, with baseline amplitude portions of the signal segment occurring before and after the R-wave sensed event signal. As such, when a tachyarrhythmia morphology is not detected and the suspected noise criteria are met, as described above, a suspected noise detection may be made.

When the gross morphology amplitude metric is greater than a predetermined threshold, "yes" branch of block 510, evidence of a tachyarrhythmia morphology is detected at block 516. In this case, detection of the tachyarrhythmia morphology may preclude determining suspected noise as described above. When the NRA is less than or equal to the NRA threshold ("no" branch of block 510), a tachyarrhythmia morphology is not detected at block 512 by control circuit 80. Control circuit 80 may determine that true tachyarrhythmia evidence criteria are unmet and determine suspected noise based on the buffered maximum peak to peak amplitudes. The NRA threshold for detecting true tachyarrhythmia evidence applied at block 510 may be set between 100 and 150, and is set to 125 in some examples, such as when 92 sample points are summed and multiplied by a weighting factor of four and normalized by the maximum absolute amplitude. The NRA threshold applied to the gross morphology amplitude metric to detect a tachyarrhythmia morphology in the cardiac electrical signal segment may depend on various factors such as the amplification and number of sample points summed, the multiplication or weighting factor of the summed sample points, etc.

Figure 10:
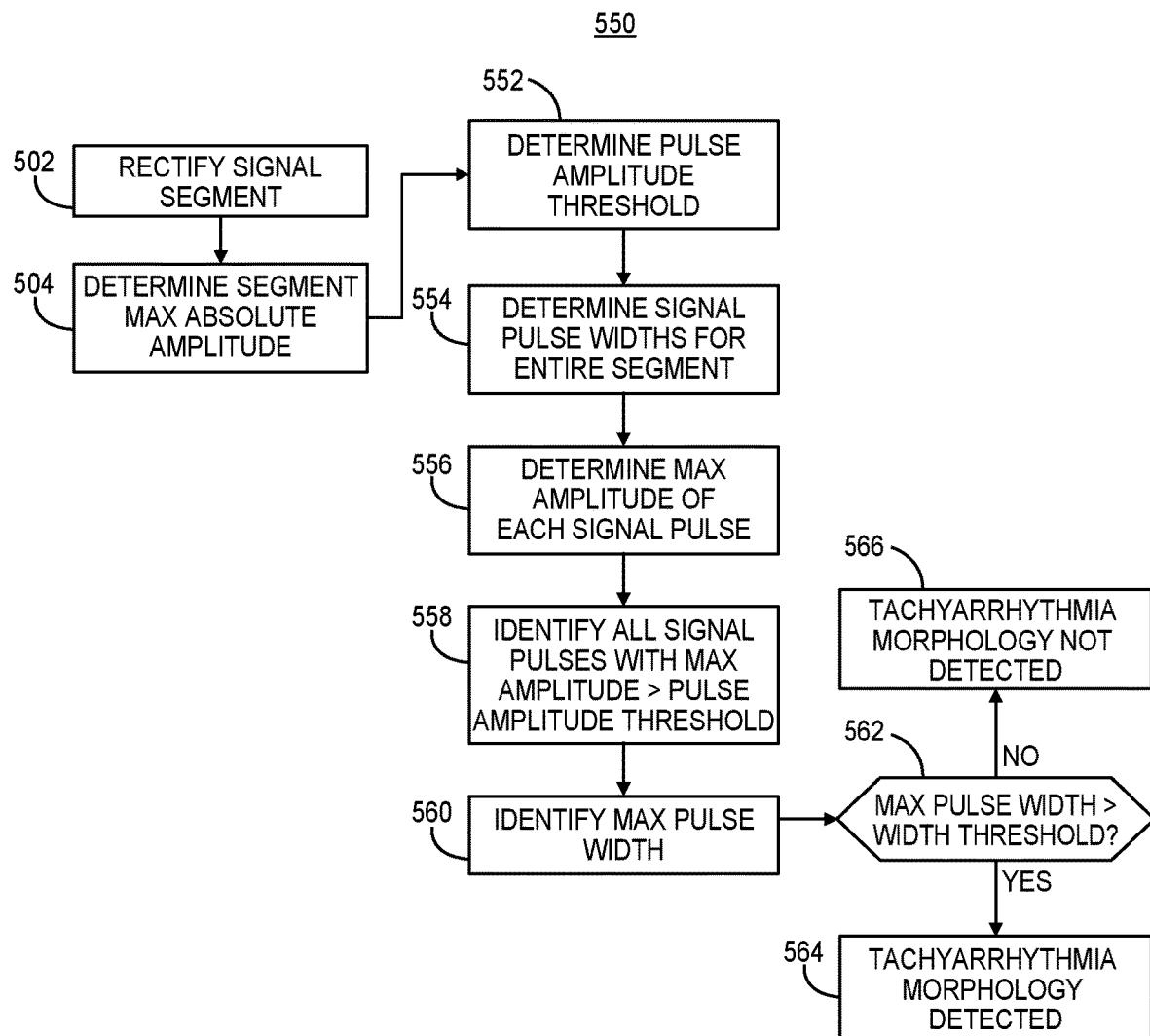
FIG. 10 is a flow chart of a method for detecting a tachyarrhythmia morphology in a cardiac electrical signal segment based on a gross morphology signal width metric according to one example.

FIG. 10 is a flow chart 550 of a method for detecting a tachyarrhythmia morphology in a cardiac electrical signal segment based on a gross morphology signal width metric according to one example. The process of flow chart 550 may be performed by control circuit 80 for determining a gross morphology signal width metric at block 316 of FIG. 7 or block 114 of FIG. 5. Blocks 502 and 504 correspond to identically-numbered blocks described above in conjunction with FIG. 9. The notch-filtered, rectified cardiac electrical signal segment, e.g., signal segment 422 shown in FIG. 8, determined at block 502 may be used to determine the maximum absolute amplitude 424 of the signal segment at block 504.

With continued reference to FIGS. 8 and 10, control circuit 80 determines a pulse amplitude threshold 426 at block 552 based on the maximum absolute amplitude 424 determined at block 504. This pulse amplitude threshold 426 may be used for identifying a signal pulse having a maximum signal width out of all signal pulses occurring during the time segment 404 of the rectified cardiac electrical signal segment 422. For example, the pulse amplitude threshold 426 used for determining the gross morphology signal width metric may be set to half the maximum absolute amplitude 424 of the rectified, notch-filtered signal segment 422.

At block 554, control circuit 80 identifies signal pulses from the cardiac electrical signal segment and determines the signal width for each signal pulse. Each signal pulse in the signal segment 422 may be identified by first identifying zero or baseline amplitude sample points 440, 442, 444, 446, 448 and 450 of the rectified signal segment 422. In other examples, the time of zero crossings of the non-rectified signal segment 402 may be identified to demarcate the signal pulses of the rectified signal segment 422 that occur between zero-crossings. In some instances, a sample point nearest to zero at a zero crossing may be set to a zero amplitude to define a baseline sample point to demarcate signal pulses. Each signal pulse during time interval 404 is identified as the sample points occurring between two consecutive baseline amplitude sample points, e.g., between points 440 and 442, between points 442 and 444, between points 444 and 446, etc. The signal width of each identified signal pulse is determined as the number of sample points (or corresponding time interval) between a pair of consecutive baseline (e.g., zero) amplitude sample points. For example, a signal pulse 432 identified between baseline points 444 and 446 has a signal width 452, the time interval (or number of sample points) between baseline points 444 and 446.

The absolute maximum amplitude of each rectified signal pulse is determined at block 556. All signal pulses of the rectified signal segment 422 that have an absolute maximum amplitude that is greater than or equal to the pulse amplitude threshold 426 are identified at block 558. For example, all signal pulses having a maximum amplitude that is at least half the maximum absolute amplitude 424 may be identified at block 558.

In the example of FIG. 8, signal pulse 432 may be the only signal pulse identified at block 558 since it is the only signal pulse that has an amplitude greater than the amplitude threshold 426. In other instances, such as in the presence of non-cardiac noise, multiple signal pulses may occur within the cardiac signal segment 422 having an amplitude greater than the amplitude threshold 426.

Control circuit 80 determines the maximum signal pulse width at block 560 out of all identified signal pulses having an amplitude greater than the pulse amplitude threshold 426. This maximum pulse width, e.g., pulse width 452 in FIG. 8, is determined as the gross morphology signal width metric for detecting a tachyarrhythmia morphology. This maximum signal pulse width 452 is expected to be the pulse width of any underlying true cardiac signal waveform in the cardiac signal segment 422.

The gross morphology signal width metric determined as the maximum pulse width 452 may be correlated to the probability of the buffered cardiac electrical signal segment 402 having a tachyarrhythmia morphology. For example, a relatively high gross morphology signal width metric may be evidence of a relatively wide ventricular fibrillation wave. Conversely, a relatively low gross morphology signal width metric may be evidence of a relatively narrow, true R-wave occurring during the time interval 404 of the cardiac electrical signal segment 402 or absence of a true cardiac signal. When a relatively wide signal pulse is not detected from the rectified cardiac electrical signal segment 422, an oversensed non-cardiac noise pulse may be present and may have triggered the buffering of the cardiac signal segment 402. Without evidence of a true tachyarrhythmia morphology (e.g., a relatively wide signal width), a tachyarrhythmia detection may be withheld to appropriately withhold therapy delivering. When evidence of a true tachyarrhythmia morphology is present, detection of the tachyarrhythmia and therapy should not be withheld.

Control circuit 80 compares the maximum pulse width 452 identified at block 560 to a pulse width threshold at block 562. In one example, the pulse width threshold is set to 20 sample points when the sampling rate is 256 Hz. When the maximum signal pulse width is less than or equal to the width threshold, control circuit 80 does not detect a tachyarrhythmia morphology at block 566. A maximum signal pulse width that is less than or equal to the width threshold may correspond to a true, relatively narrow R-wave, e.g., during a sinus rhythm or to a non-cardiac noise pulse. Control circuit 80 may apply suspected noise criteria at block 314 of FIG. 7 when the maximum signal pulse width is less than or equal to the width threshold.

When the maximum pulse width is greater than the width threshold at block 562, the relatively wide maximum signal pulse width may be detected as evidence of a true tachyarrhythmia waveform morphology at block 564. Evidence of the tachyarrhythmia morphology in signal segment 402, which may correspond to the greatest maximum amplitude in the maximum amplitude buffer, may preclude a determination of suspected noise, even when the maximum amplitudes in the amplitude buffer meet the suspected noise criteria.

In various examples, both the gross morphology amplitude metric and the gross morphology signal width metric may be determined (e.g., at block 316 of FIG. 7 or block 114 of FIG. 5 according to the techniques of FIG. 9 and FIG. 10) and compared to respective threshold values. In some examples, one of the gross morphology amplitude metric or the gross morphology signal width metric may be required to be less than or equal to the respective threshold value for evidence of a true tachyarrhythmia morphology to not be detected, enabling a suspected noise determination to be made by control circuit 80. When both of the gross morphology amplitude and the gross morphology signal width are greater than the respective tachyarrhythmia morphology threshold value, evidence of a tachyarrhythmia morphology may be detected in the cardiac electrical signal segment, precluding determination of suspected noise. In other examples, both of the gross morphology amplitude and signal width metric may be required to be less than or equal to the respective threshold value in order to determine evidence of a true tachyarrhythmia morphology is not met and allow determination of suspected noise. If one of the gross morphology metrics, e.g., the amplitude or width metric, is greater than or equal to the respective tachyarrhythmia morphology threshold value, the tachyarrhythmia morphology evidence criteria may be met at block 318 of FIG. 7, preventing control circuit 80 from determining suspected noise criteria are met.

The gross morphology amplitude metric determined by the method of FIG. 9 and the gross morphology signal width metric determined by the method of FIG. 10 may be used in combination to detect evidence of a true tachyarrhythmia morphology at block 318 of FIG. 7 to prevent detection of noise when the underlying rhythm is likely to be a true tachyarrhythmia. A segment of the cardiac electrical signal that has a relatively high gross morphology amplitude metric and/or relatively high gross morphology signal width metric is evidence of a true tachyarrhythmia morphology and prevents noise detection that may lead to withholding of a tachyarrhythmia detection and subsequent therapy in order to maintain a high sensitivity to tachyarrhythmia detection.

Figure 11:
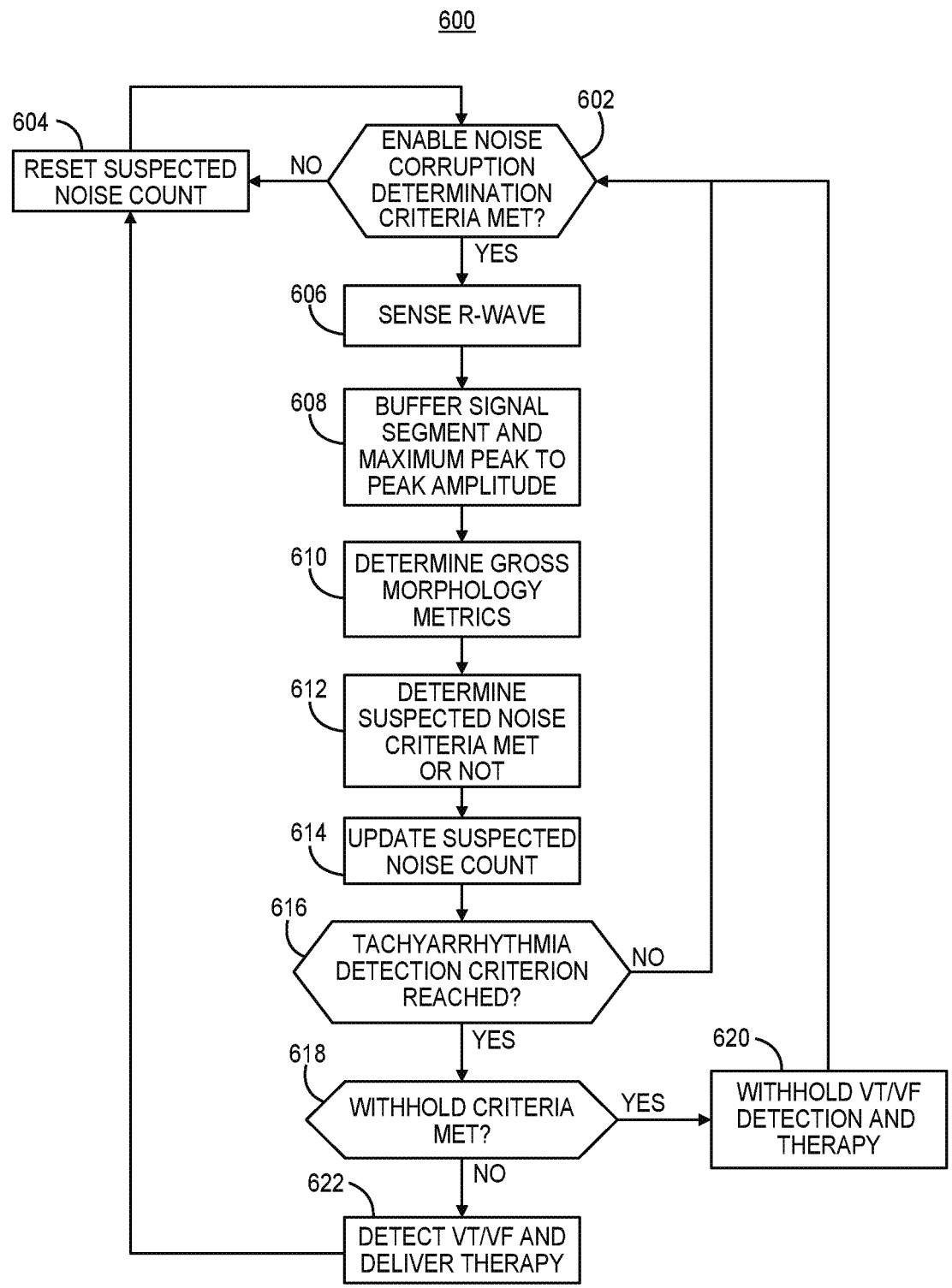
FIG. 11 is a flow chart of a method for controlling tachyarrhythmia detection and therapy by a medical device according to one example.

FIG. 11 is a flow chart 600 of a method for controlling tachyarrhythmia detection and therapy by a medical device according to one example. At block 602, control circuit 80 of ICD 14 may determine if criteria for enabling signal analysis for determining noise corruption are met. In one example, the criteria for enabling analysis for determining noise corruption requires counting a threshold number of tachyarrhythmia intervals by control circuit 80. For instance, a threshold number of VT and/or VF intervals may trigger signal analysis for determination of noise corruption, where the threshold number is less than the NID required to detect VT or VF. For instance, a count of three, five, eight or another selected number of RRIs determined by timing circuit 90 that fall into the VT and/or VF interval zones may be required to enable signal analysis for noise corruption determination at block 602.

When the criteria for enabling analysis for determining noise corruption are met at block 602, control circuit 80 buffers a cardiac electrical signal segment at block 608 in response to the currently sensed R-wave (block 606). Control circuit 80 determines the maximum peak to peak amplitude from the buffered signal segment at block 608. In some examples, the cardiac electrical signal segment is buffered from the second cardiac electrical signal from second sensing channel 85 when the R-wave is sensed by the first sensing channel 83 from the first cardiac electrical signal. In other examples, the cardiac electrical signal segment may be buffered from the same cardiac electrical signal from which the R-wave was sensed. The maximum peak to peak amplitude is stored with an associated timestamp and/or RRI.

At block 610, control circuit 80 may determine gross morphology metrics from the buffered signal segment to store in conjunction with the associated maximum peak to peak amplitude. In this way the data for determining noise corruption is available from each buffered signal segment if needed. The buffered signal segment may be overwritten by the next buffered signal segment with just the maximum peak to peak amplitude, gross morphology metrics and timestamp or RRI stored in respective data buffers for a desired number of R-wave sensed event signals, e.g., 11 to 13 consecutive R-wave sensed event signals. The gross morphology metrics may be determined by control circuit 80 at block 610 according to the techniques described above in conjunction with FIGS. 8-10.

At block 612, control circuit 80 determines if the suspected noise criteria are met or not based on the buffered data. For example, control circuit 80 may first determine suspected true cardiac event intervals between maximum peak to peak amplitudes stored in the amplitude buffer that are greater than a threshold amplitude as described in conjunction with FIG. 7. Control circuit 80 may determine whether true tachyarrhythmia interval evidence criteria are met. In response to true tachyarrhythmia interval evidence criteria being met, control circuit 80 may determine whether the true tachyarrhythmia morphology evidence criteria are met by the gross morphology metrics buffered in the data buffers in association with at least the greatest maximum peak to peak amplitude stored in the amplitude buffer. In response to both the true tachyarrhythmia interval evidence criteria being met and the true tachyarrhythmia morphology evidence criteria being met, control circuit 80 may determine that suspected noise criteria are not met at block 612. Control circuit 80 updates the suspected noise count at block 614 accordingly.

When at least one of the true tachyarrhythmia interval evidence criteria or the true tachyarrhythmia morphology criteria are not met, control circuit 80 may determine whether the buffered maximum peak to peak amplitudes meet the suspected noise criteria at block 612. Based on whether the suspected noise criteria are met by the buffered maximum peak to peak amplitudes, control circuit 80 may update the suspected noise count at block 614. As described above, control circuit 80 may determine that suspected noise criteria are met when at least one maximum peak to peak amplitude is less than a noise threshold amplitude and the ratio of the lowest maximum peak to peak amplitude to the greatest maximum peak to peak amplitude is less than a ratio threshold. In other examples, a ratio of the greatest post-notch filtered peak to peak amplitude to the associated pre-notch filtered peak to peak amplitude may be compared to a relative noise ratio threshold to determine suspected noise criteria are met at block 612. In some examples, at least one of the interval-based or morphology-based true tachyarrhythmia evidence criteria is not met by the buffered data in order for the suspected noise criteria to be met. In other examples, both of the interval-based and morphology based true tachyarrhythmia evidence criteria may be required to be unmet in order for the suspected noise criteria to be met at block 612.

While the flow charts presented herein may suggest a particular order of applying the true tachyarrhythmia evidence criteria and the suspected noise criteria, the processes performed by control circuit 80 for determining when criteria are met or not may be performed in a different order than shown in the example flow charts presented herein. Furthermore, the processes performed for determining when criteria are met may be performed simultaneously in parallel processes to arrive at an outcome for updating the suspected noise count at block 614 based on whether true tachyarrhythmia criteria are met (or not) and suspected noise criteria are met (or not).

An X of Y counter may be implemented in control circuit 80 that is updated with each new determination of suspected noise criteria being met or unmet. For example, a first-in-first-out buffer in memory 82 may set a flag indicating suspected noise criteria are met. The buffer may store a value (e.g., 1=suspected noise criteria met and 0=suspected noise criteria not met) for each of a predetermined number of buffer locations, e.g., six to fifteen locations.

At block 616, control circuit 80 may determine when one or more tachyarrhythmia detection criteria are met. In some examples, tachyarrhythmia detection criteria applied at block 616 may include an interval-based criterion, such as a required NID being reached by the VT interval counter, VF interval counter, or a combined VT/VF interval counter of tachyarrhythmia detection circuit 92. In other examples, the tachyarrhythmia detection criteria determined to be met or unmet at block 616 may be based on QRS waveform morphology meeting morphology-based criteria or a combination of interval or rate-based criteria and morphology-based tachyarrhythmia detection criteria.

When no tachyarrhythmia detection criteria are met at block 616, control circuit 80 may return to block 602 to continue performing signal analysis for determining suspected noise corruption as long as the criteria for enabling noise corruption determination remains satisfied at block 602. When the criteria for enabling signal analysis for noise detection becomes unmet (e.g., the VT and/or VF interval count falls below a respective threshold for enabling noise corruption determination), the counter or buffer of the suspected noise determinations may be cleared at block 604. For example, a buffer storing zeros and ones corresponding to suspected noise criteria being unmet or met may be cleared to all zeros at block 604. After clearing the suspected noise count, control circuit 80 returns to block 602 to wait for the noise corruption determination criteria to be met again.

When at least one criterion for detecting tachyarrhythmia is determined to be satisfied at block 616, control circuit 80 may compare the current suspected noise count to withhold criteria at block 618. For example, when the number of suspected noise determinations reaches or exceeds a withhold threshold, the withhold criteria may be met, and the tachyarrhythmia detection based on at least one satisfied tachyarrhythmia detection criterion is withheld by control circuit 80 at block 620. VT or VF is not detected by control circuit 80 at block 620 when the NID is reached, for example, and a threshold number of suspected noise determinations have been made out of the most recent Y sensed event signals. In some examples, a single suspected noise determination may meet withhold criteria. In other examples, at least three out of twelve buffered values in a suspected noise buffer may be required to be ones, indicating suspected noise criteria have been met three times out of the most recent twelve times the buffered data has been analyzed for determining suspected noise.

When the withhold criteria are met, a tachyarrhythmia therapy that is programmed to be delivered in response to VT or VF detection is not scheduled or delivered. In other examples, the VT or VF detection may be made in response to tachyarrhythmia detection criteria being satisfied at block 616, but the therapy may be withheld at block 620 when the withhold criteria are met at block 618. Control circuit 80 may return to block 602 to continue buffering data and analyzing the data for noise corruption as long as the noise corruption determination criteria are met at block 602.

When the withhold criteria are not met at block 618, e.g., when the suspected noise count is less than a withhold threshold, the tachyarrhythmia is detected at block 622 by control circuit 80 based on the tachyarrhythmia detection criterion being met at block 616. Therapy, e.g., ATP and/or CV/DF shock, may be delivered in response to the tachyarrhythmia detection at block 622. Control circuit 80 may advance to block 604 to reset the suspected noise count after detecting VT/VF and delivering therapy and wait at block 602 until noise corruption determination criteria are met again.

Figure 12:
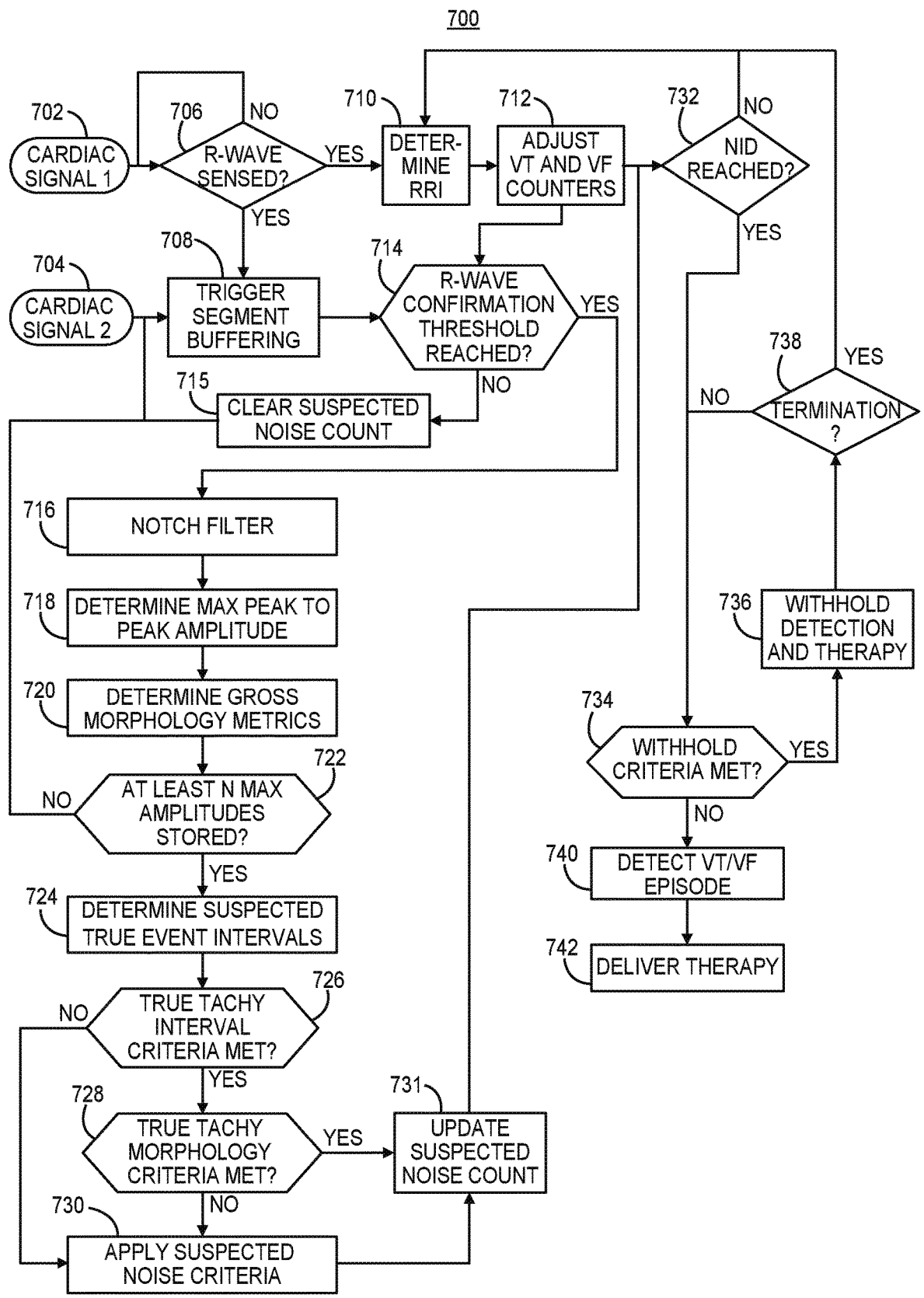
FIG. 12 is a flow chart of a method performed by a medical device for detecting non-cardiac noise corruption of a cardiac signal and rejecting a ventricular tachyarrhythmia detection in response to determining noise corruption according to another example.

FIG. 12 is a flow chart 700 of a method performed by ICD 14 for detecting noise corruption of a cardiac signal and rejecting a ventricular tachyarrhythmia detection in response to determining noise corruption according to another example. At blocks 702 and 704, two different cardiac electrical signals may be sensed by sensing circuit 86. In some examples, two different sensing electrode vectors may be selected by sensing circuit 86 for receiving a first cardiac electrical signal by a first sensing channel 83 and a second cardiac electrical signal by a second sensing channel 85, respectively. The two sensing electrode vectors may be selected by switching circuitry included in sensing circuit 86 under the control of control circuit 80. In some examples, the two sensing electrode vectors are programmed by a user and retrieved from memory 82 by control circuit 80 and passed to sensing circuit 86 as vector selection control signals.

In some examples, the first sensing electrode vector selected for sensing the first cardiac electrical signal at block 702 may be a relatively short bipole, e.g., between electrodes 28 and 30 or between electrodes 28 and 24 of lead 16 or other electrode combinations as described above. The relatively short bipole may include electrodes that are in relative close proximity to each other and to the ventricular heart chambers to provide sensing of a relatively "near-field" ventricular signal for sensing R-waves compared to a second sensing vector selected at block 704. The first sensing electrode vector may be a vertical sensing vector (with respect to an upright or standing position of the patient) or approximately aligned with the cardiac axis for maximizing the amplitude of R-waves in the first cardiac electrical signal for reliable R-wave sensing. The first sensing electrode vector, however, is not limited to any particular interelectrode spacing or orientation and may be selected as any available electrode pair. The first cardiac electrical signal sensed at block 702 may be a narrow band filtered signal for enhancing the quality of R-wave signals in the first cardiac electrical signal.

The second sensing electrode vector used to receive a second cardiac electrical signal at block 704 may be a relatively longer bipole having an inter-electrode distance that is greater than the first sensing electrode vector. For example, the second sensing electrode vector may be selected as the vector between one of the pace sense electrodes 28 or 30 and ICD housing 15, one of defibrillation electrodes 24 or 26 and housing 15 or other combinations of one electrode along the distal portion of the lead 16 and the housing 15. This second sensing electrode vector may be orthogonal or almost orthogonal to the first sensing electrode vector in some examples, but the first and second sensing vectors are not required to be orthogonal vectors. The second sensing electrode vector may receive a relatively more global or far-field cardiac electrical signal compared to the first sensing electrode vector. The second cardiac electrical signal sensed by the second sensing channel 85 at block 704 may be analyzed by control circuit 80 for detecting noise corruption of both of the first and second cardiac electrical signals based on the analysis of only the second cardiac electrical signal. The second cardiac electrical signal may be a wide band filtered signal.

In other examples, the first and second cardiac electrical signals sensed at blocks 702 and 704 may be received from the same sensing electrode vector, such that a single cardiac electrical signal is received by the sensing circuit 86, but the raw, received signal may be processed by two different sensing channels 83 and 85 of sensing circuit 86 having different filtering and/or other signal processing features to sense two different cardiac electrical signals, one, e.g., a narrow band filtered signal, used by the first sensing channel 83 for sensing R-waves and one, e.g., a wide band filtered signal, sensed by the second sensing channel 85 for determining noise corruption including performing tachyarrhythmia morphology analysis. In still other examples, a single cardiac signal is used for sensing R-waves and buffered for detecting noise corruption of the cardiac signal.

Sensing circuit 86 may produce an R-wave sensed event signal at block 706 in response to the first sensing channel 83 detecting an R-wave sensing threshold crossing by the first cardiac electrical signal. The R-wave sensed event signal may be passed to control circuit 80. In response to the R-wave sensed event signal, down-going "yes" branch of block 706, control circuit 80 is triggered at block 708 to store a segment of the second cardiac electrical signal received from the second sensing channel 85 over a predetermined time interval. Segments of the second cardiac electrical signal may be stored in a circulating buffer of memory 82 configured to store multiple sequential segments, where storage of each segment is triggered by an R-wave sensed event signal produced by the first sensing channel 83. A digitized segment of the second cardiac electrical signal may be 100 to 500 ms long, for example, including sample points before and after the time of the R-wave sensed event signal. The segment of the second cardiac electrical signal may or may not be centered in time on the R-wave sensed event signal received from sensing circuit 86. For instance, the segment may extend 100 ms after the R-wave sensed event signal and be 200 to 500 ms in duration such that the segment extends from about 100 to 400 ms before the R-wave sensed event signal to 100 ms after. In other examples, the segment may be centered on the R-wave sensed event signal or extend a greater number of sample points after the R-wave sensed event signal than before. In one example, the buffered segment of the cardiac electrical signal is at least 48 sample points obtained at a sampling rate of 256 Hz, or about 188 ms. In another example, the buffered segment is at least 92 sample points, or approximately 360 ms, sampled at 256 Hz.

Memory 82 may be configured to store a predetermined number of second cardiac electrical segments, e.g., at least 1 and in some cases two or more cardiac electrical signal segments, in circulating buffers such that the oldest segment is overwritten by the newest segment. However, previously stored segments may never be analyzed for determining noise corruption and may be overwritten if an R-sense confirmation threshold is not reached at block 714 as described below. In some examples, at least one segment of the second cardiac electrical signal may be stored and if not needed for detecting noise (before noise corruption determination criteria are met), the segment is overwritten by the next segment corresponding to the next R-wave sensed event signal.

In addition to buffering a segment of the second cardiac electrical signal, control circuit 80 responds to the R-wave sensed event signal produced at block 706 by determining an RRI at block 710 ending with the current R-wave sensed event signal and beginning with the most recent preceding R-wave sensed event signal. The timing circuit 90 of control circuit 80 may pass the RRI timing information to the tachyarrhythmia detection circuit 92 which adjusts tachyarrhythmia interval counters at block 712. If the RRI is longer than a tachycardia detection interval (TDI), the tachyarrhythmia interval counters remain unchanged. If the RRI is shorter than the TDI but longer than a fibrillation detection interval (FDI), e.g., if the RRI is in a tachycardia detection interval zone, a VT interval counter is increased at block 712. If the RRI is shorter than or equal to the FDI, a VF interval counter is increased at block 712. In some examples, a combined VT/VF interval counter is increased if the RRI is less than the TDI.

After updating the tachyarrhythmia interval counters at block 712, tachyarrhythmia detector 92 compares the counter values to an R-sense confirmation threshold at block 714 to determine if noise corruption determination criteria are met. Tachyarrhythmia detector 92 also compares the counter values to VT and VF detection thresholds at block 732 to determine if a respective NID is met. If a VT or VF detection interval counter has reached an R-sense confirmation threshold, "yes" branch of block 714, control circuit 80 may begin analysis of the second cardiac electrical signal to determine if noise corruption is likely causing false R-wave sensed event signals to be produced by the first sensing channel 83, resulting in VT and/or VF counters being increased at block 712. The R-sense confirmation threshold may be a VT or VF interval count value that is greater than one or another higher threshold count value, indicating that a tachycardia may be suspected but has not yet reached a detection threshold. Different R-sense confirmation thresholds may be applied to the VT interval counter and the VF interval counter. For example, the R-sense confirmation threshold may be a count of two on the VT interval counter and a count of three on the VF interval counter. In other examples, the R-sense confirmation threshold is a higher number, for example five or higher, but may be less than the number of VT or VF intervals required to detect VT or VF. In addition or alternatively to applying an R-sense confirmation threshold to the individual VT and VF counters, an R-sense confirmation threshold may be applied to a combined VT/VF interval counter. It is recognized that in some examples, VT detection may not be enabled and VF detection may be enabled. In this case, only a VF interval counter is updated at block 712 in response to RRI determinations, and the R-sense confirmation threshold may be applied to the VF interval counter at block 714.

If the R-sense confirmation threshold is not reached by any of the tachyarrhythmia interval counters at block 714, the control circuit 80 waits for the next R-wave sensed event signal at block 708 to buffer the next segment of the second cardiac electrical signal. If the R-sense confirmation threshold is reached at block 714, e.g., when the VF interval counter is greater than 2, the control circuit 80 begins analysis of the buffered second cardiac electrical signal segments for detecting noise corruption.

At block 716, control circuit 80 may notch filter the buffered signal segment. In other examples, the second sensing channel 85 may include a notch filter such that a notch filtered signal segment is buffered at block 708. However, both the wide band filtered signal prior to notch filtering and the notch filtered signal may be used in the analysis for determining noise corruption in some examples. Both the wide band filtered signal and the wideband and notch filtered signal may be buffered at block 708 or the wide band filtered signal may be buffered and subsequently notch filtered at block 716 using hardware, firmware or software. As described above, the notch-filter may be implemented to attenuate 50 Hz and/or 60 Hz line frequency noise (and in some cases harmonics thereof).

At block 718, control circuit 80 determines the maximum peak to peak amplitude from at least the notch filtered signal segment. In some examples, the maximum peak to peak amplitude is determined from a portion of the notch filtered signal segment. For example, if the signal segment buffered at block 708 is 300 ms or longer, e.g., 360 ms, the maximum peak to peak amplitude may be determined from a portion of the signal segment encompassing the time of the associated R-wave sensed event signal, e.g., from a 150 to 200 ms segment. In one example, the maximum peak to peak amplitude is determined as the difference between the maximum sample point amplitude and the minimum sample point amplitude that occur during a 188 ms segment that encompasses the time of the associated R-wave sensed event signal.

In some examples, control circuit 80 may determine the maximum peak to peak amplitude from the post-notch filtered signal segment and from the pre-notch filtered signal segment at block 718. The determination of both enables control circuit 80 to determine a ratio of the post- to pre-notch filtered maximum peak to peak amplitudes for comparison to a relative noise threshold for detecting suspected noise at block 730. In other examples, only the maximum peak to peak amplitude of the notch filtered segment is determined at block 718.

At block 720, control circuit 80 may determine the gross morphology metric(s) for determining when tachyarrhythmia morphology evidence criteria are met at block 728. The gross morphology metrics may be determined as generally described in conjunction with FIGS. 9 and 10 above. The post-notch filtered maximum peak to peak amplitude, the timestamp or associated RRI, the gross morphology metrics, and in some examples the pre-notch filtered maximum peak to peak amplitude may all be stored in data buffers in memory 82. Control circuit 80 may determine if the required minimum number of buffered maximum peak to peak amplitudes have been stored at block 722 to proceed with the noise corruption determination. If not, control circuit 80 returns to block 708 to obtain additional cardiac electrical signal segment data as long as the R-sense confirmation threshold is met. In some examples, the amplitude buffer must be filled with at least three maximum peak to peak amplitudes in order to advance to determine noise corruption. If the minimum is met at block 722, control circuit 80 advances to block 724.

At block 724, control circuit 80 determines suspected true event intervals based on the buffered maximum peak to peak amplitudes. Determination of whether true tachyarrhythmia interval criteria are met is based at least on the greatest maximum peak to peak amplitude stored in the amplitude buffer. As described above in conjunction with FIG. 7, control circuit 80 may identify buffered maximum peak to peak amplitudes that are greater than a threshold amplitude set based on the greatest maximum peak to peak amplitude. Control circuit may determine one or more suspected true event intervals between the identified maximum peak to peak amplitudes. When at least one suspected true event interval falls within a specified interval range, or when only a single buffered maximum peak to peak amplitude is greater than the threshold amplitude, control circuit 80 may determine that true tachyarrhythmia interval evidence criteria are met at block 726. If at least one suspected true event interval is determined and no suspected true event intervals fall within the specified interval range, control circuit 80 may advance directly to block 730 to determine if suspected noise criteria are met.

When the true tachyarrhythmia interval criteria are met at block 726, control circuit 80 determines whether the buffered gross morphology metrics meet true tachyarrhythmia morphology criteria at block 728. As described above, the gross morphology metric(s) associated with a greatest maximum peak to peak amplitude stored in the maximum amplitude buffer may be compared to respective threshold(s). For example, when both of the gross morphology amplitude metric and the gross morphology signal width metric associated with the greatest maximum peak to peak amplitudes are greater than a respective threshold, true tachyarrhythmia morphology criteria are met at block 728. Control circuit 80 advances to block 731 to update a suspected noise count (e.g., by moving a zero into a suspected noise buffer) indicating that suspected noise is not determined based on the currently buffered maximum peak to peak amplitudes and associated data. Since the true tachyarrhythmia interval criteria and the true tachyarrhythmia morphology criteria are both satisfied, suspected noise is not determined based on the currently buffered data without comparing the buffered maximum peak to peak amplitudes to the suspected noise criteria at block 730.

Control circuit 80 may determine that at least one of the gross morphology amplitude metric or the gross morphology signal width metric is less than or equal to a respective threshold at block 728. In this case, control circuit 80 may determine that the true tachyarrhythmia morphology criteria are not met. When true tachyarrhythmia interval criteria are met (block 726) but true tachyarrhythmia morphology criteria are unmet, control circuit 80 applies suspected noise criteria to the buffered maximum peak to peak amplitude data at block 730. In the example shown, the true tachyarrhythmia interval criteria is required to be met at block 726 before applying the true tachyarrhythmia morphology criteria at block 728. In other examples, however, control circuit 80 may require that the true tachyarrhythmia morphology criteria be met before checking if the true tachyarrhythmia interval criteria are met. In still other examples, both the true tachyarrhythmia interval and morphology criteria may be applied and if either are unmet, suspected noise criteria may be applied at block 730. In still other examples, control circuit 80 may determine whether the suspected noise criteria are met at block 730 and, if met, control circuit 80 may verify that at least one of the true tachyarrhythmia interval criteria or the true tachyarrhythmia morphology criteria are unmet before detecting suspected noise based on the buffered maximum peak to peak amplitudes. The criteria applied at blocks 726, 728 and 730, therefore, may be applied in a different order than shown or applied in parallel in order to determine whether to increase the suspected noise count at block 731 or not.

At block 730, control circuit 80 compares buffered maximum peak to peak amplitudes to the suspected noise criteria. As described above, the suspected noise criteria may require that a lowest maximum peak to peak amplitude (which may be determined as the mean or median of two or more smallest maximum peak to peak amplitudes) is less than a noise threshold amplitude. Additionally or alternatively, the suspected noise criteria may require that the ratio of the lowest maximum peak to peak amplitude to the greatest maximum peak to peak amplitude is less than a threshold ratio. Additionally or alternatively, the suspected noise criteria may require that a ratio of the post-notch filtered maximum peak to peak amplitude to the pre-notch filtered maximum peak to peak amplitude for at least one buffered maximum amplitude is less than a relative noise threshold.

When control circuit 80 determines that the buffered maximum peak to peak amplitude data meets the suspected noise criteria at block 730, control circuit 80 increases a suspected noise count at block 731. As described above, the noise count may be increased by moving a one into a suspected noise buffer configured to store a predetermined number of ones or zeros for facilitating counting the number of times suspected noise criteria are met over the most recent, predetermined number of R-wave sensed event signals. In some examples, the suspected noise counter is configured to store up to twelve values, ones or zeros, to facilitate determining the number of times the suspected noise criteria are met over the most recent twelve R-wave sensed event signals. It is noted, that the current R-wave sensed event signal may or may not be a suspected noise signal. The determination of noise criteria being met at block 730 may be based on any of the buffered maximum peak to peak amplitudes meeting the suspected noise criteria.

After updating the suspected noise count at block 731, control circuit 80 may determine if the NID has been reached by the VT, VF or combined VT/VF interval counters at block 732. When a threshold number of intervals to detect (NID) is not reached by the VT interval counter, VF interval counter, or combined VT/VF interval counter, control circuit 80 returns to block 710 to continue determining Rills and analyzing second cardiac electrical signal segments as long as the R-sense confirmation threshold is satisfied (block 714). If the R-sense confirmation threshold is no longer met at block 714, the suspected noise counter may be cleared at block 715, e.g., by setting all values in a suspected noise buffer to zeros.

When the NID is reached at block 732, based on the values of the VT and/or VF interval counters, control circuit 80 determines whether a withhold detection threshold number of suspected noise determinations has been reached (or exceeded) at block 734. The VT or VF detection based on the NID being reached is withheld at block 736 in response to a withhold threshold number of suspected noise determinations. In one example, if at least three out of twelve values in the suspected noise buffer are one, indicating at least three suspected noise determinations based on the buffered maximum peak to peak amplitude data over the most recent twelve R-wave sensed event signals, control circuit 80 determines noise corruption, and the withhold criteria are met at block 734. The VT or VF detection (and any associated VT or VF therapy) based on the NID being reached is withheld by control circuit 80 at block 736. While not explicitly shown by the flow chart 700 for the sake of clarity, as long as the NID continues to be met at block 732, control circuit 80 may continue to determine whether suspected noise criteria are met at blocks 716 through 730 as new R-waves are sensed and update the suspected noise count at block 731.

In some examples, control circuit 80 may determine if termination criteria are met at block 738 when detection has been withheld based on the determination of noise corruption (withhold criteria met at block 734). Termination of the fast rhythm may be detected based on a predetermined number of RRIs that are greater than a tachyarrhythmia detection interval or when a mean, median or other metric of RRIs determined over predetermined time interval is greater than a tachyarrhythmia detection interval. For example, when a threshold number of RRIs longer than the VT detection interval (e.g., when VT detection is enabled) or longer than the VF detection interval (e.g., when VT detection is not enabled) are detected subsequent to the NID being met, tachyarrhythmia termination may be detected at block 738. In one example, termination is detected at block 738 when at least eight consecutive long RRIs, e.g., greater than the VT detection interval, are detected. In another example, control circuit 80 may detect termination at block 738 when a predetermined time interval elapses and a median RRI is greater than the VT detection interval. For instance, when the median RRI of the most recent 12 RRIs is always greater than the VT detection interval for at least 20 seconds, or other predetermined time period, control circuit 80 may detect termination at block 738. Control circuit 80 may reset the VT and VF interval counters and the suspected noise count and return to block 710 in response to detecting termination.

When the NID is met at block 732 and the withhold criteria are not met at block 734, e.g., due to the suspected noise count being less than a threshold number, a VT or VF episode is detected at block 740. Therapy delivery circuit 84 may deliver a VT or VF therapy at block 742 in response to the VT/VF detection. It is to be understood that other criteria besides the NID criterion may be applied by control circuit 80 before detecting the VT or VF at block 740. For example, various P-wave oversensing rejection criteria, T-wave oversensing rejection criteria, supraventricular tachycardia (SVT) rejection criteria, etc. may be required to be unmet and/or tachyarrhythmia onset criteria, tachyarrhythmia morphology criteria, or other tachyarrhythmia criteria may be required to be met before detecting VT/VF at block 740 and delivering therapy at block 742.

It is contemplated that in other examples, the VT/VF detection may be made in response to detection criteria being satisfied, e.g., the NID being reached at block 732, but the VT/VF therapy may be withheld at block 736 when the withhold criteria is met or exceeded by the suspected noise count. Therapy delivery circuit 84 may withhold a VT or VF therapy until the withhold criteria is no longer met and the tachyarrhythmia is still being detected. Therapy delivery circuit 84 may deliver a withheld therapy when the withhold criteria are no longer met and termination of the detected VT or VF has not been detected at block 738. If the detected VT or VF is determined to be terminated at block 738 while the therapy is being withheld, the suspected noise count and VT/VF interval counters may all be cleared, and the process may return to block 710 without ever delivering a therapy.

It should be understood that, depending on the example, certain acts or events of any of the methods described herein can be performed in a different sequence, may be added, merged, or left out altogether (e.g., not all described acts or events are necessary for the practice of the method). Moreover, in certain examples, acts or events may be performed concurrently, e.g., through multi-threaded processing, interrupt processing, or multiple processors, rather than sequentially. In addition, while certain aspects of this disclosure are described as being performed by a single circuit or unit for purposes of clarity, it should be understood that the techniques of this disclosure may be performed by a combination of units or circuits associated with, for example, a medical device.

In one or more examples, the functions described may be implemented in hardware, software, firmware, or any combination thereof. If implemented in software, the functions may be stored as one or more instructions or code on a computer-readable medium and executed by a hardware-based processing unit. Computer-readable media may include computer-readable storage media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPLAs), or other equivalent integrated or discrete logic circuitry. Accordingly, the term "processor," as used herein may refer to any of the foregoing structure or any other structure suitable for implementation of the techniques described herein. Also, the techniques could be fully implemented in one or more circuits or logic elements.

Thus, a medical device has been presented in the foregoing description with reference to specific examples. It is to be understood that various aspects disclosed herein may be combined in different combinations than the specific combinations presented in the accompanying drawings. It is appreciated that various modifications to the referenced examples may be made without departing from the scope of the disclosure and the following claims.

What is claimed is:

1. A medical device comprising:
   a sensing circuit configured to sense at least one cardiac electrical signal and sense event signals from the at least one cardiac electrical signal; and
   a control circuit coupled to the sensing circuit and configured to:
   determine a maximum amplitude associated with each of a plurality of the sensed event signals;
   identify a greatest maximum amplitude from the determined maximum amplitudes associated with the plurality of the sensed event signals;
   determine at least one tachyarrhythmia metric based on at least the identified greatest maximum amplitude;
   determine the at least one tachyarrhythmia metric does not meet true tachyarrhythmia evidence criteria;
   determine that suspected noise criteria are met based on the determined maximum amplitudes;
   determine that a tachyarrhythmia detection criterion is met based on event signals sensed by the sensing circuit; and
   in response to determining that the true tachyarrhythmia evidence criteria are not met and that the suspected noise criteria are met, withhold a tachyarrhythmia detection when the tachyarrhythmia detection criterion is determined to be met.

2. The device of claim 1, wherein the control circuit is configured to:
   set a threshold amplitude based on the greatest maximum amplitude;
   identify each of the maximum amplitudes that are greater than the threshold amplitude;
   determine the at least one tachyarrhythmia metric by determining a suspected true event interval based on each of the maximum amplitudes identified to be greater than the threshold amplitude; and
   determine that the at least one tachyarrhythmia metric does not meet true tachyarrhythmia criteria by determining that the suspected true event interval does not fall within a predetermined interval range.

3. The device of claim 1, further comprising a memory configured to buffer a cardiac electrical signal segment in response to each of the plurality of the sensed event signals;
   wherein the control circuit is configured to:
   determine at least one tachyarrhythmia metric by determining at least one gross morphology metric from the buffered cardiac electrical signal segment associated with the greatest maximum amplitude;
   determine that the at least one tachyarrhythmia metric does not meet true tachyarrhythmia evidence criteria by determining that the at least one gross morphology metric is less than or equal to a threshold.

4. The device of claim 3, wherein the control circuit is configured to determine the at least one gross morphology metric by:
   determining a summation of absolute amplitudes of sample points of the buffered cardiac electrical signal segment;
   determining a maximum absolute amplitude of the buffered cardiac electrical signal segment; and
   determining the at least one gross morphology metric by dividing the summation of sample points by the maximum absolute amplitude.

5. The device of claim 3, wherein the control circuit is configured to determine the at least one gross morphology metric by determining a maximum pulse width of the buffered cardiac electrical signal segment.

6. The device of claim 3, wherein the control circuit is configured to:
   determine at least one gross morphology metric by determining a gross morphology amplitude metric from the buffered cardiac electrical signal segment associated with the greatest maximum amplitude and determining a gross morphology signal width metric from the buffered cardiac electrical signal segment associated with the greatest maximum amplitude; and
   determine the at least one tachyarrhythmia metric does not meet true tachyarrhythmia criteria by determining that at least one of the gross morphology amplitude metric is less than or equal to a first threshold or the gross morphology signal width metric is less than or equal to a second threshold.

7. The device of claim 1, wherein:
   the sensing circuit is configured to:
   sense a first cardiac electrical signal and a second cardiac electrical signal; and
   sense event signals from the first cardiac electrical signal; and
   the control circuit is configured determine the maximum amplitudes and the at least one tachyarrhythmia metric from the second cardiac electrical signal.

8. The device of claim 7, wherein:
   the sensing circuit comprises:
   a narrowband filter having a first bandpass for sensing the first cardiac electrical signal;
   a wideband filter having a second bandpass wider than the first bandpass for sensing the second cardiac electrical signal; and
   a notch filter for filtering the second cardiac electrical signal;

the control circuit is configured to determine the maximum amplitude associated with each of the plurality of the sensed event signals by determining a maximum peak to peak amplitude of the notch filtered second cardiac electrical signal.

9. The device of claim 1, wherein the control circuit is configured to determine that suspected noise criteria are met based on the determined maximum amplitudes by determining that at least one of the maximum amplitudes is less than a noise threshold amplitude.

10. The device of claim 1, wherein the control circuit is configured to determine that suspected noise criteria are met based on the determined maximum amplitudes by determining that a ratio of a lowest maximum amplitude determined from the maximum amplitudes to a greatest maximum amplitude determined from the maximum amplitudes is less than a threshold ratio.

11. The device of claim 1, wherein:
the sensing circuit comprises a notch filter for filtering at least one cardiac electrical signal;
the control circuit is configured to determine that suspected noise criteria are met based on the determined maximum amplitudes by:
determining a first maximum amplitude from the at least one cardiac electrical signal;
determining a second maximum amplitude from the at least one cardiac electrical signal after notch filtering;
determining a ratio of the second maximum amplitude to the first maximum amplitude;
determining that the ratio is less than a relative noise threshold.

12. The device of claim 1, further comprising a therapy delivery circuit configured to deliver a tachyarrhythmia therapy, wherein:
the control circuit is further configured to detect tachyarrhythmia by:
determining that the tachyarrhythmia detection criterion is met based on event signals sensed by the sensing circuit; and
determining that at least one of:
the true tachyarrhythmia evidence criteria are met by the at least one tachyarrhythmia metric; or
the suspected noise criteria are not met by the maximum amplitudes; and
the therapy delivery circuit is configured to deliver a therapy in response to the control circuit detecting the tachyarrhythmia.

13. A method, comprising:
sensing at least one cardiac electrical signal;
sensing event signals from the at least one cardiac electrical signal;
determining a maximum amplitude associated with each of a plurality of the sensed event signals;
identifying a greatest maximum amplitude from the determined maximum amplitudes associated with the plurality of the sensed event signals;
determining at least one tachyarrhythmia metric based on at least the identified greatest maximum amplitude;
determining the at least one tachyarrhythmia metric does not meet true tachyarrhythmia evidence criteria;
determining that suspected noise criteria are met based on the determined maximum amplitudes;
determining that a tachyarrhythmia detection criterion is met based on the plurality of sensed event signals; and
in response to determining that the true tachyarrhythmia evidence criteria are not met and that the suspected noise criteria are met, withholding a tachyarrhythmia detection when the tachyarrhythmia detection criterion is determined to be met.

14. The method of claim 12, further comprising:
setting a threshold amplitude based on the greatest maximum amplitude;
identifying each of the maximum amplitudes that are greater than the threshold amplitude;
determining the at least one tachyarrhythmia metric by determining a suspected true event interval based on each of the maximum amplitudes identified to be greater than the threshold amplitude; and
determining that the at least one tachyarrhythmia metric does not meet true tachyarrhythmia evidence criteria by determining that the suspected true event interval does not fall within a predetermined interval range.

15. The method of claim 13, further comprising:
buffering a cardiac electrical signal segment in response to each of the plurality of the sensed event signals;
determining at least one tachyarrhythmia metric by determining at least one gross morphology metric from the buffered cardiac electrical signal segment associated with the greatest maximum amplitude;
determining that the at least one tachyarrhythmia metric does not meet true tachyarrhythmia evidence criteria by determining that the at least one gross morphology metric is less than or equal to a threshold.

16. The method of claim 15, wherein determining the at least one gross morphology metric comprises:
determining a summation of absolute amplitudes of sample points of the buffered cardiac electrical signal segment;
determining a maximum absolute amplitude of the buffered cardiac electrical signal segment; and
determining the at least one gross morphology metric by dividing the summation of sample points by the maximum absolute amplitude.

17. The method of claim 15, wherein determining the at least one gross morphology metric comprises determining a maximum pulse width of the buffered cardiac electrical signal segment.

18. The method of claim 15, comprising:
determining at least one gross morphology metric by determining a gross morphology amplitude metric from the buffered cardiac electrical signal segment associated with the greatest maximum amplitude and determining a gross morphology signal width metric from the buffered cardiac electrical signal segment associated with the greatest maximum amplitude; and
determining the at least one tachyarrhythmia metric does not meet true tachyarrhythmia criteria by determining that at least one of the gross morphology amplitude metric is less than or equal to a first threshold or the gross morphology signal width metric is less than or equal to a second threshold.

19. The method of claim 13, comprising
sensing a first cardiac electrical signal and a second cardiac electrical signal;
sensing event signals from the first cardiac electrical signal; and
determining the maximum amplitudes and the at least one tachyarrhythmia metric from the second cardiac electrical signal.

20. The method of claim 19, comprising:
sensing the first cardiac electrical signal comprises filtering by a narrowband filter having a first bandpass;

sensing the second cardiac electrical signal comprises filtering by a wideband filter having a second bandpass wider than the first bandpass; and notch filtering the second cardiac electrical signal; and determining the maximum amplitude associated with each of the plurality of the sensed event signals by determining a maximum peak to peak amplitude of the notch filtered second cardiac electrical signal.

21. The method of claim 13, wherein determining that suspected noise criteria are met based on the determined maximum amplitudes comprises determining that at least one of the maximum amplitudes is less than a noise threshold amplitude.

22. The method of claim 13, wherein determining that suspected noise criteria are met based on the determined maximum amplitudes comprises determining that a ratio of a lowest maximum amplitude determined from the maximum amplitudes to a greatest maximum amplitude determined from the maximum amplitudes is less than a threshold ratio.

23. The method of claim 13, wherein determining that suspected noise criteria are met based on the determined maximum amplitudes comprises:
   determining a first maximum amplitude from the at least one cardiac electrical signal;
   notch filtering at least one cardiac electrical signal;
   determining a second maximum amplitude from the at least one cardiac electrical signal after notch filtering;
   determining a ratio of the second maximum amplitude to the first maximum amplitude; and
   determining that the ratio is less than a relative noise threshold.

24. The method of claim 13, further comprising:
   determining that the tachyarrhythmia detection criterion is met based on the sensed event signals;
   detecting the tachyarrhythmia in response to determining at least one of:
      the true tachyarrhythmia evidence criteria are met by the at least one tachyarrhythmia metric; or
      the suspected noise criteria are not met by the maximum amplitudes; and
   delivering a therapy in response to the tachyarrhythmia detection.

25. A non-transitory computer-readable medium storing a set of instructions which, when executed by a control circuit of a medical device, cause the medical device to:
   sense at least one cardiac electrical signal;
   sense event signals from the at least one cardiac electrical signal;
   determine a maximum amplitude associated with each of a plurality of the sensed event signals;
   identify a greatest maximum amplitude from the determined maximum amplitudes associated with the plurality of the sensed event signals;
   determine at least one tachyarrhythmia metric based on at least the identified greatest maximum amplitude;
   determine the at least one tachyarrhythmia metric does not meet true tachyarrhythmia evidence criteria;
   determine that suspected noise criteria are met based on the determined maximum amplitudes;
   determine that a tachyarrhythmia detection criterion is met based on the sensed event signals; and
   in response to determining that the true tachyarrhythmia evidence criteria are not met and that the suspected noise criteria are met, withhold a tachyarrhythmia detection when the tachyarrhythmia detection criterion is determined to be met.

* * * * *